United States Patent
Chen et al.

(10) Patent No.: US 10,060,880 B2
(45) Date of Patent: Aug. 28, 2018

(54) MAGNETORESISTIVE (MR) SENSORS EMPLOYING DUAL MR DEVICES FOR DIFFERENTIAL MR SENSING

(71) Applicant: QUALCOMM Incorporated, San Diego, CA (US)

(72) Inventors: Wei-Chuan Chen, San Diego, CA (US); Jung Pill Kim, San Diego, CA (US); Seung Hyuk Kang, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 113 days.

(21) Appl. No.: 15/266,342

(22) Filed: Sep. 15, 2016

(65) Prior Publication Data

US 2018/0074016 A1 Mar. 15, 2018

(51) Int. Cl.
G01N 27/74 (2006.01)
G01R 33/09 (2006.01)
B82Y 25/00 (2011.01)

(52) U.S. Cl.
CPC ............ *G01N 27/745* (2013.01); *B82Y 25/00* (2013.01); *G01R 33/09* (2013.01); *G01R 33/093* (2013.01); *G01R 33/098* (2013.01)

(58) Field of Classification Search
CPC .... G01N 27/745; G01R 33/098; G01R 33/09; G01R 33/093; B82Y 25/00
See application file for complete search history.

(56) References Cited

U.S. PATENT DOCUMENTS

| 6,204,071 B1 * | 3/2001 | Ju ........................ B82Y 10/00 360/327.32 |
| 6,807,033 B2 * | 10/2004 | Zhu ....................... B82Y 10/00 360/324 |

(Continued)

FOREIGN PATENT DOCUMENTS

| WO | 03054523 A2 | 7/2003 |
| WO | 2006059270 A2 | 6/2006 |

(Continued)

OTHER PUBLICATIONS

Dixit, Chandra K. et al., "Protein Microarrays with Novel Microfluidic Methods: Current Advances," Microarrays, vol. 3, No. 3, Jul. 1, 2014, pp. 180-202.

(Continued)

*Primary Examiner* — Tung X Nguyen
*Assistant Examiner* — Dominic Hawkins
(74) *Attorney, Agent, or Firm* — W&T/Qualcomm

(57) ABSTRACT

Magnetoresistive (MR) sensors employing dual MR devices for differential MR sensing are provided. These MR sensors may be used as biosensors to detect the presence of biological materials as an example. An MR sensor includes dual MR sensor devices that may be tunnel magnetoresistive (TMR) devices or giant magnetoresistive (GMR) devices as examples. The MR devices are arranged such that a channel is formed between the MR devices for receiving magnetic nanoparticles. A magnetic stray field generated by the magnetic nanoparticles causes free layers in the MR devices to rotate in opposite directions, thus causing differential resistances between the MR devices for greater sensing sensitivity. Further, as another aspect, by providing the channel between the MR devices, the magnetic stray field generated by the magnetic nanoparticles can more easily rotate the (Continued)

magnetic moment orientation of the free layers in the MR devices, thus further increasing sensitivity.

23 Claims, 11 Drawing Sheets

(56) References Cited

U.S. PATENT DOCUMENTS

| | | | | |
|---|---|---|---|---|
| 6,961,225 B2* | 11/2005 | Gill | ............ | B82Y 10/00 360/324.11 |
| 7,085,111 B2* | 8/2006 | Freitag | ............ | G11B 5/3932 360/322 |
| 7,336,452 B2* | 2/2008 | Dovek | ............ | B82Y 10/00 360/324.1 |
| 2006/0128035 A1* | 6/2006 | Coehoorn | ............ | B82Y 25/00 436/524 |
| 2008/0074802 A1* | 3/2008 | Carey | ............ | B82Y 25/00 360/324.1 |
| 2009/0065359 A1* | 3/2009 | Zhou | ............ | B82Y 25/00 204/556 |
| 2010/0079135 A1* | 4/2010 | Ando | ............ | B82Y 25/00 324/207.11 |
| 2011/0241664 A1 | 10/2011 | Zhang | | |
| 2012/0169331 A1 | 7/2012 | Wang et al. | | |

FOREIGN PATENT DOCUMENTS

| | | |
|---|---|---|
| WO | 2010098884 A1 | 9/2010 |
| WO | 2013040489 A1 | 3/2013 |

OTHER PUBLICATIONS

Han, Shu-Jen et al., "Magnetic Nanotechnology for Biodetection," Journal of Laboratory Automation, vol. 15, No. 2, Apr. 2010, pp. 93-98.

Krishna, Venkatramana D. et al., "Giant Magnetoresistance-based Biosensor for Detection of Influenza A Virus," Frontiers in Microbiology, vol. 7, No. 400, Mar. 2016, 8 pages.

Wang, Shan X. et al., "Advances in Giant Magnetoresistance Biosensors With Magnetic Nanoparticle Tags: Review and Outlook," IEEE Transactions on Magnetics, vol. 44, No. 7, Jul. 2008, pp. 1687-1702.

Wu, Jing et al., "Microfluidic sensing: state of the art fabrication and detection techniques," Journal of Biomedical Optics, vol. 16, No. 8, Aug. 2011, 13 pages.

Kim, Jung Pill et al., "A 45nm 1Mb Embedded STT-MRAM with design techniques to minimizeread-disturbance," 2011 Symposium on VLSI Circuits Digest of Technical Papers, Jun. 15-17, 2011, IEEE, pp. 296-297.

International Search Report and Written Opinion for PCT/US2017/047317, dated Oct. 23, 2017, 12 pages.

* cited by examiner

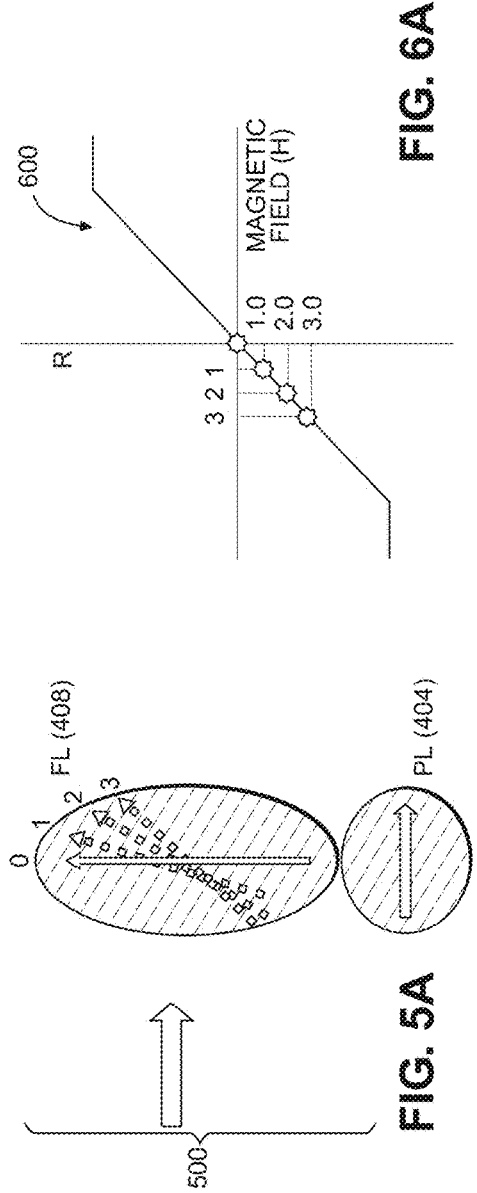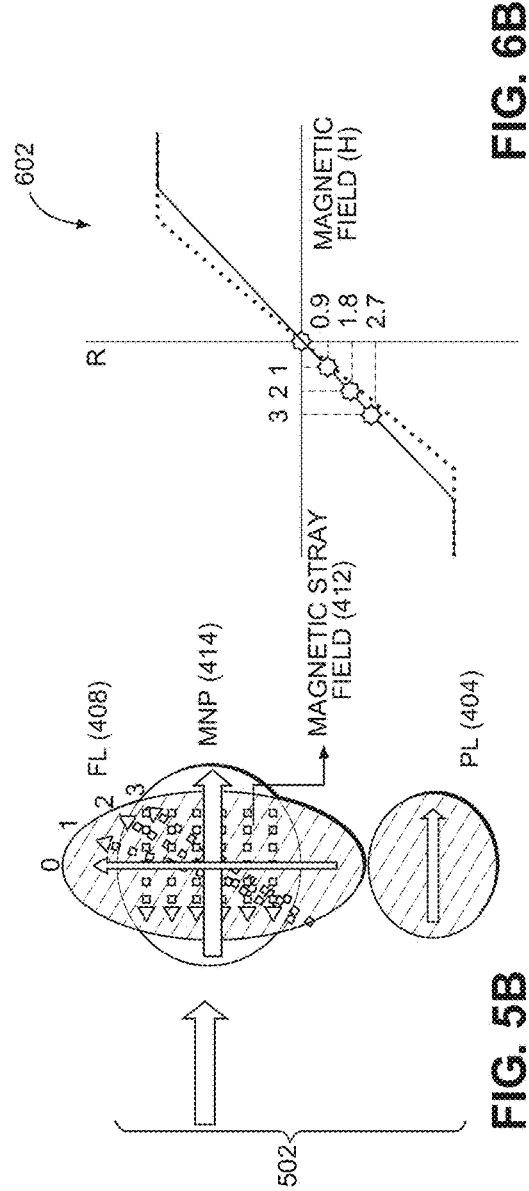

MAGNETORESISTIVE (MR) SENSORS EMPLOYING DUAL MR DEVICES FOR DIFFERENTIAL MR SENSING

BACKGROUND

I. Field of the Disclosure

The technology of the disclosure relates generally to magnetoresitive (MR) devices, and more particularly to use of MR devices as MR sensors, such as biosensors, for detecting the presence of magnetic nanoparticles.

II. Background

It may be desired in health care and other related fields to be able to detect the presence of a target analyte in a biological sample for diagnosing, monitoring, and/or maintaining health and wellness. Detecting target analytes may also be desired for performing certain health care related applications, such as human genotyping, bacteriological screening, and biological and pharmacological research. In this regard, biosensing systems can be employed to detect the presence of a target analyte in a biological sample for such applications. Biosensors are employed in biosensing systems to detect the presence of target analytes. A biosensor consists of two (2) components: a bioreceptor and a transducer. A bioreceptor is a biomolecule that recognizes the target analyte. The transducer converts the recognition event of the target analyte into a measurable signal based on a change that occurs from the bioreceptor in reaction in the presence of the target analyte. For example, a biosensor could be provided that measures glucose concentration in a blood sample by simply dipping the biosensor in the sample. This is in contrast to a conventional assay in which many steps are used and wherein each step may require a reagent to treat the sample. The simplicity and the speed of measurement is a main advantage of a biosensor. Biosensors can be provided in many different forms including non-invasive, in vitro, transcutaneous, ingested (e.g., a pill), and as a wearable or surgically implanted device.

FIG. 1 illustrates an exemplary biosensing system 100 that employs a biosensor for detecting a presence and/or properties of a biological sample. A biological sample 102 to be tested is obtained or prepared. The biological sample 102 is a sensitive biological element (e.g., tissue, microorganisms, organelles, cell receptors, enzymes, antibodies, nucleic acids, etc.) and is a biologically derived material or biomimetic component that interacts (binds or recognizes) with the target analyte under study. Examples of biological samples include cell cultures, human samples, food samples, and environmental samples. The biological sample 102 is then processed to separate a target analyte 104 of interest (e.g., a certain molecule, nucleotide, protection, and metal ion). The target analyte 104 is then introduced to target bioreceptors 106 that are designed to interact with the specific target analyte 104 of interest to produce an effect measurable by a transducer. Unbound analytes are washed away.

One type of biosensor that has been developed to detect a target analyte of interest is a magnetoresistive (MR) biosensor. MR biosensors include a transducer that is configured to recognize a magnetic field change as a function of sensed resistance. In this regard, as shown in FIG. 1, high magnetization magnetic or superparamagnetic nanoparticles 108 (hereinafter "magnetic nanoparticles 108") can be introduced and captured by the target bioreceptors 106 that are bound to the target analyte 104. The magnetic nanoparticles 108 can then be introduced to a MR sensor 110 to detect the presence of the magnetic nanoparticles 108. The MR sensor 110 measures the magnetic field change as a result of introduction of the magnetic nanoparticles 108 as function of a change in resistance. The MR sensor 110 generates a signal 112 representing this change in resistance that can be analyzed by a sensing circuit 114 to determine the presence of the target analyte 104 in the target bioreceptor 104.

One type of MR sensing technology that can be employed in biosensing applications is a giant magnetoresistive (GMR) biosensor, such as a GMR sensor 200 shown in FIG. 2. The GMR sensor 200 can be fabricated using standard complementary metal-oxide (MOS) semiconductor (CMOS) fabrication technology. The GMR effect of the GMR sensor 200 originates from its spin-dependent scattering, which depends on a relative spin of a carrier and scattering site. In this regard, the GMR sensor 200 includes a GMR device 202 that includes a pinned layer 204, a non-magnetic metal spacer 206, and a free layer 208 that has a fixed magnetization. The pinned layer 204 is formed on a substrate 210 and is comprised of a metal material (e.g., a Cobalt (Co) material) that has a fixed horizontal magnetization in the X direction, which is in-plane to the GMR device 202. The metal spacer 206, such as a Copper (Cu) spacer, is disposed above the pinned layer 204. The free layer 208 is disposed above the metal spacer 206. The free layer 208 has a magnetization that can rotate freely based on the change in a magnetic stray field 212 applied to the free layer 208. The magnetic stray field 212 is provided by the magnetization of magnetic nanoparticles 214 passing in a channel 216 (e.g., a microfluidic channel) in the GMR sensor 200, thereby forming a biological active area that is captured by bioreceptors bound to a target analyte to be detected. The channel 216 may be formed in a passivation layer 218 of a biochip 220 above a metal cap layer 222 such that the channel 216 is externally accessible from the internal components of the biochip 220 that forms a microfluidic device. For example, the magnetic nanoparticles 214 may be in a fluid form that is disposed in the channel 216. An external magnetic field 224, such as from an external coil, is applied longitudinal or perpendicular to the channel 216 to align and saturate the magnetic moments of the magnetic nanoparticles 214. Thus, when the magnetic nanoparticles 214 pass in the channel 216 above the free layer 208 of a first polarity, the magnetic stray field 212 of the magnetic nanoparticles 214 induces a change in the magnetic moment in the free layer 208. For example, the magnetic stray field 212 may only disturb the magnetic moment of the free layer 208 such that the magnetic moment rotates in as little as one (1) degree. This change in the magnetic moment of the free layer 208 causes a change in resistance of the GMR device 202. This change in resistance resulting from disturbing the magnetic moment of the free layer 208 can be determined based on sensing a voltage change in the GMR device 202. For example, a sense current $Is_1$ can be directed to flow through the metal spacer 206 and the free layer 208, and between metal lines 226(1), 226(2) to measure the voltage across the metal lines 226(1), 226(2) based on the resistance of the GMR device 202 according to Ohm's law.

While the GMR device 202 in FIG. 2 can be used as a biosensor, several issues exist. The GMR device 202 may be difficult to scale down due to its current-in-plane (CIP) design. In the CIP design, the metal lines 226(1), 226(2) are disposed at the top of the GMR sensor 200. The metal lines 226(1), 226(2) may have a minimum pitch due to fabrication limitations that cannot be scaled down. Further, the external magnetic field 224 is also required beyond the biochip 220. Further, MR ratio of the GMR device 202 may be low, such as less than 25%, thereby providing a lower signal-to-noise ratio (SNR) of resistance change between the presence and lack of presence of magnetic nanoparticles 214 resulting in a lower sensitivity device. A strong magnetic stray field 212 in the magnetic nanoparticles 214 and/or the presence of more magnetic nanoparticles 214 could improve the SNR of the GMR device 202. However, the channel 216 is separated from the free layer 208 by the passivation layer 218 and the metal cap layer 222. Further, the working temperature of the GMR device 202 may be lower, because the metal spacer 206 may otherwise diffuse into the pinned and free layers 204, 208, thereby changing the MR properties of the GMR device 202.

SUMMARY OF THE DISCLOSURE

Aspects of the present disclosure involve magnetoresistive (MR) sensors employing dual MR devices for differential MR sensing. For example, these MR devices may be used as biosensors to detect the presence of biological materials. The MR devices can be provided in a biosensor chip fabricated using semiconductor fabrication methods as an example. In certain aspects, a MR sensor is provided that includes dual MR devices. The MR sensors may be tunnel magnetoresistive (TMR) devices or giant magnetoresistive (GMR) devices as examples. The MR sensors are arranged such that a channel is formed between the MR devices for receiving magnetic nanoparticles. The channel may provide a biological active area that allows magnetic nanoparticles to pass that have been captured by bioreceptors bound to target analytes of interest to be detected. A magnetic stray field generated by the magnetic nanoparticles causes the magnetic moment of the free layers in the MR devices to rotate in opposite directions, thus causing differential resistances between the MR devices for greater sensing sensitivity. The differential resistances can be measured and amplified, if desired, to provide a larger sense differential resulting from the change in the magnetic moment of the free layers due to the presence of the magnetic nanoparticles. Further, as another aspect, by providing the channel between the MR devices, the magnetic stray field generated by the magnetic nanoparticles can more easily rotate the magnetic moment orientations (i.e., magnetization) of the free layers in the MR devices for a given stray magnetic strength due to reduced distance between the free layers and the magnetic nanoparticles, thereby further increasing the signal-to-noise ratio (SNR) of the MR sensor. Even further, in another aspect, additional magnetic hard bias layers can be provided within the MR devices (e.g., in the same stack structure) adjacent to the channel to generate a magnetic bias field in the channel to align magnetic moments of the magnetic nanoparticles in the channel and allow for an on-biosensor chip. This is opposed to, for example, having to provide an external magnetic field generated by an external source.

In this regard, in one exemplary aspect, a MR sensor is provided. The MR sensor comprises a first MR device disposed in an encapsulation material, the first MR device having a first resistance. The MR sensor also comprises a second MR device disposed in the encapsulation material a horizontal distance away from the first MR device, the second MR device having a second resistance. The MR sensor also comprises an external channel formed in a void in the encapsulation material between the first MR device and the second MR device, the external channel configured to capture magnetic nanoparticles. The first resistance of the first MR device is configured to increase in response to a presence of the magnetic nanoparticles in the external channel exerting a magnetic stray field on the first MR device. The second resistance of the second MR device is configured to decrease in response to the presence of the magnetic nanoparticles in the external channel exerting the magnetic stray field on the second MR device.

In another exemplary aspect, a MR sensor is provided. The MR sensor comprises a first means for providing a first MR resistance disposed in an encapsulation material. The MR sensor also comprises a second means for providing a second MR resistance disposed in the encapsulation material a horizontal distance away from the first means for providing the first MR resistance. The MR sensor also comprises a means for capturing external magnetic nanoparticles between the first means for providing the first MR resistance and the second means for providing the second MR resistance. The first means for providing the first MR resistance increases in resistance in response to the presence of the magnetic nanoparticles in an external channel exerting a magnetic stray field on the first means for providing the first MR resistance. The second means for providing the second MR resistance decreases in resistance in response to the presence of the magnetic nanoparticles in the external channel exerting the magnetic stray field on the second means for providing the second MR resistance.

In another exemplary aspect, a MR sensing system is provided. The MR sensing system comprises a plurality of MR sensors. Each MR sensor among the plurality of MR sensors comprises a first MR device disposed in an encapsulation material, the first MR device having a first resistance. Each MR sensor among the plurality of MR sensors also comprises a second MR device disposed in the encapsulation material a horizontal distance away from the first MR device, the second MR device having a second resistance. Each MR sensor among the plurality of MR sensors comprises an external channel formed in a void in the encapsulation material between the first MR device and the second MR device, the external channel configured to capture magnetic nanoparticles. The first resistance of the first MR device is configured to increase in response to a presence of the magnetic nanoparticles in the external channel exerting a magnetic stray field on the first MR device. The second resistance of the second MR device is configured to decrease in response to the presence of the magnetic nanoparticles in the external channel exerting the magnetic stray field on the second MR device. The MR sensing system also comprises a sensing circuit. The sensing circuit is configured to select a MR sensor among the plurality of MR sensors in response to a sense operation. The sensing circuit is also configured to generate a first sensed voltage based on a change in the first resistance of the first MR device of the selected MR sensor. The sensing circuit is configured to generate a second sensed voltage based on a change in the second resistance of the second MR device of the selected MR sensor. The MR sensing system also comprises a sense amplifier. The sense amplifier is configured to generate a differential output voltage indicative of the presence of the magnetic nanoparticles in the external channel based on a difference between the first sensed voltage and the second sensed voltage.

In another exemplary aspect, a method of detecting a presence of magnetic nanoparticles in a MR sensor is provided. The method comprises receiving magnetic nanoparticles bound to a bioreceptor configured to capture a target analyte of interest in a MR biosensor chip in at least one external channel among a plurality of external channels each forming a biological active area. The MR biosensor chip comprises a plurality of MR sensors each comprising a first MR device disposed in an encapsulation material, the first MR device having a first resistance, and a second MR device disposed in the encapsulation material a horizontal distance away from the first MR device, the second MR device having a second resistance. The at least one external channel among the plurality of external channels is formed in a void in the encapsulation material between the first MR device and the second MR device, and is configured to capture the magnetic nanoparticles. The first resistance of the first MR device is configured to increase in response to a presence of the magnetic nanoparticles in the at least one external channel exerting a magnetic stray field on the first MR device. The second resistance of the second MR device is configured to decrease in response to the presence of the magnetic nanoparticles in the at least one external channel exerting the magnetic stray field on the second MR device. The method also comprises selecting at least one MR sensor among the plurality of MR sensors in response to a sense operation. The method also comprises generating a first sensed voltage based on a change in the first resistance of the first MR device of the selected at least one MR sensor. The method also comprises generating a second sensed voltage based on a change in the second resistance of the second MR device of the selected at least one MR sensor. The method also comprises generating a differential output voltage indicative of the presence of the magnetic nanoparticles in the at least one external channel based on a difference between the first sensed voltage and the second sensed voltage

BRIEF DESCRIPTION OF THE FIGURES

FIGS. 5A and 5B are diagrams illustrating exemplary magnetization of a free layer in a TMR device in FIG. 4 when a magnetic stray field is not present from magnetic nanoparticles, and when a magnetic stray field is generated in the presence of magnetic nanoparticles, respectively;

FIGS. 6A and 6B are graphs illustrating exemplary magnetization of a free layer in the TMR sensor in FIG. 4 when a magnetic bias field is generated by a hard magnetic layer in a TMR device in the TMR sensor outside the presence of magnetic nanoparticles, and in the presence of magnetic nanoparticles, respectively;

DETAILED DESCRIPTION

Figure 1:
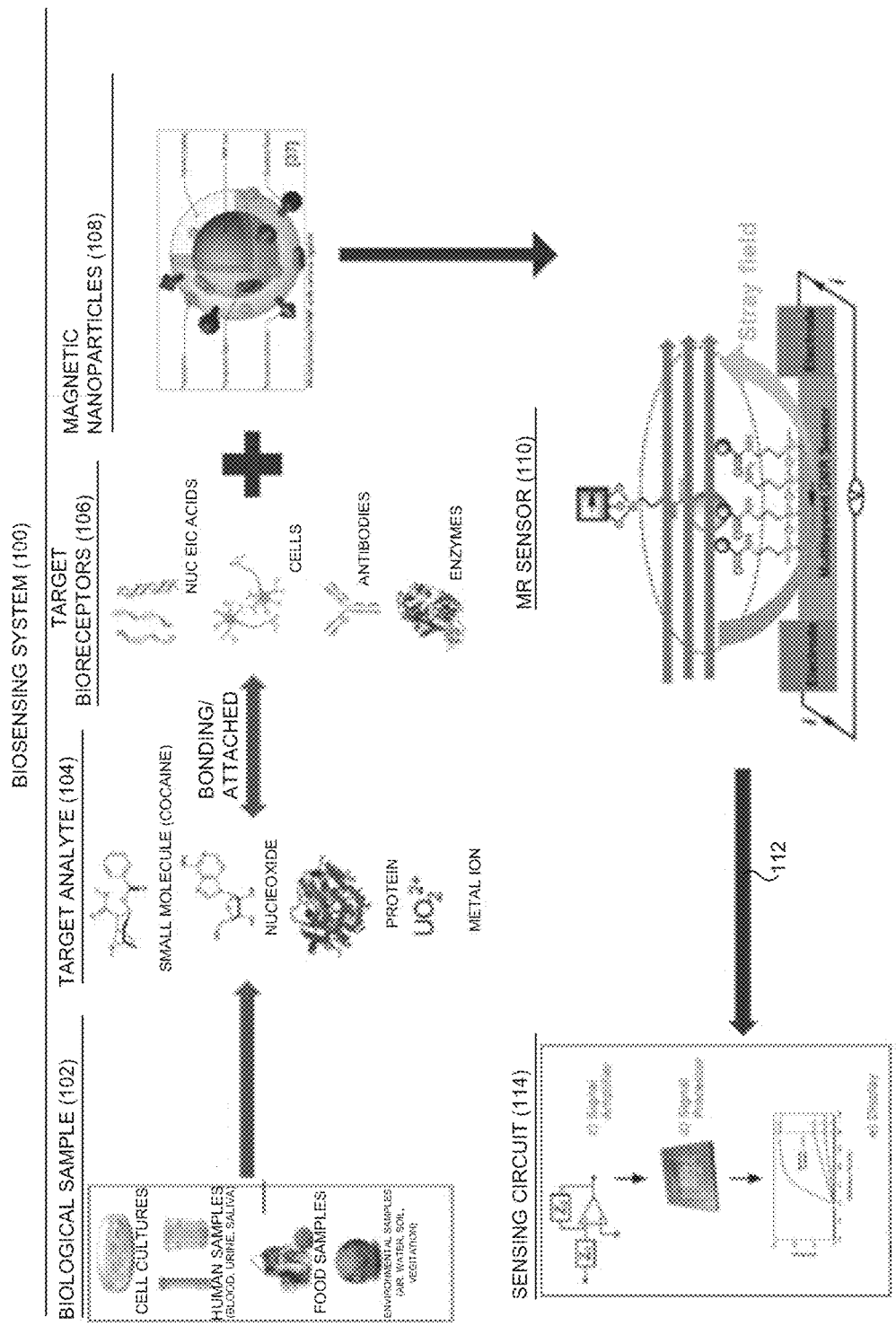
FIG. 1 is a schematic diagram of a biosensing system that employs a biosensor for detecting presence and/or properties of a biological sample.

With reference now to the drawing figures, several exemplary aspects of the present disclosure are described. The word "exemplary" is used herein to mean "serving as an example, instance, or illustration." Any aspect described herein as "exemplary" is not necessarily to be construed as preferred or advantageous over other aspects.

Aspects of the present disclosure involve magnetoresistive (MR) sensors employing dual MR devices for differential MR sensing. For example, these MR devices may be used as biosensors to detect the presence of biological materials. The MR devices can be provided in a biosensor chip fabricated using semiconductor fabrication methods as an example. In certain aspects, a MR sensor is provided that includes dual MR devices. The MR sensors may be tunnel magnetoresistive (TMR) devices or giant magnetoresistive (GMR) devices as examples. The MR sensors are arranged such that a channel is formed between the MR devices for receiving magnetic nanoparticles. The channel may provide a biological active area that allows magnetic nanoparticles to pass that have been captured by bioreceptors bound to target analytes of interest to be detected. A magnetic stray field generated by the magnetic nanoparticles causes the magnetic moment of the free layers in the MR devices to rotate in opposite directions, thus causing differential resistances between the MR devices for greater sensing sensitivity. The differential resistances can be measured and amplified, if desired, to provide a larger sense differential resulting from the change in the magnetic moment of the free layers due to the presence of the magnetic nanoparticles. Further, as another aspect, by providing the channel between the MR devices, the magnetic stray field generated by the magnetic nanoparticles can more easily rotate the magnetic moment orientations of the free layers in the MR devices for a given stray magnetic strength due to reduced distance between the free layers and the magnetic nanoparticles, thereby further increasing the signal-to-noise ratio (SNR) of the MR sensor. Even further, in another aspect, additional magnetic hard bias layers can be provided within the MR devices (e.g., in the same stack structure) adjacent to the channel to generate a magnetic bias field in the channel to align magnetic moments of the magnetic nanoparticles in the channel and allow for an on-biosensor chip. This is opposed to, for example, having to provide an external magnetic field generated by an external source.

Figure 3:
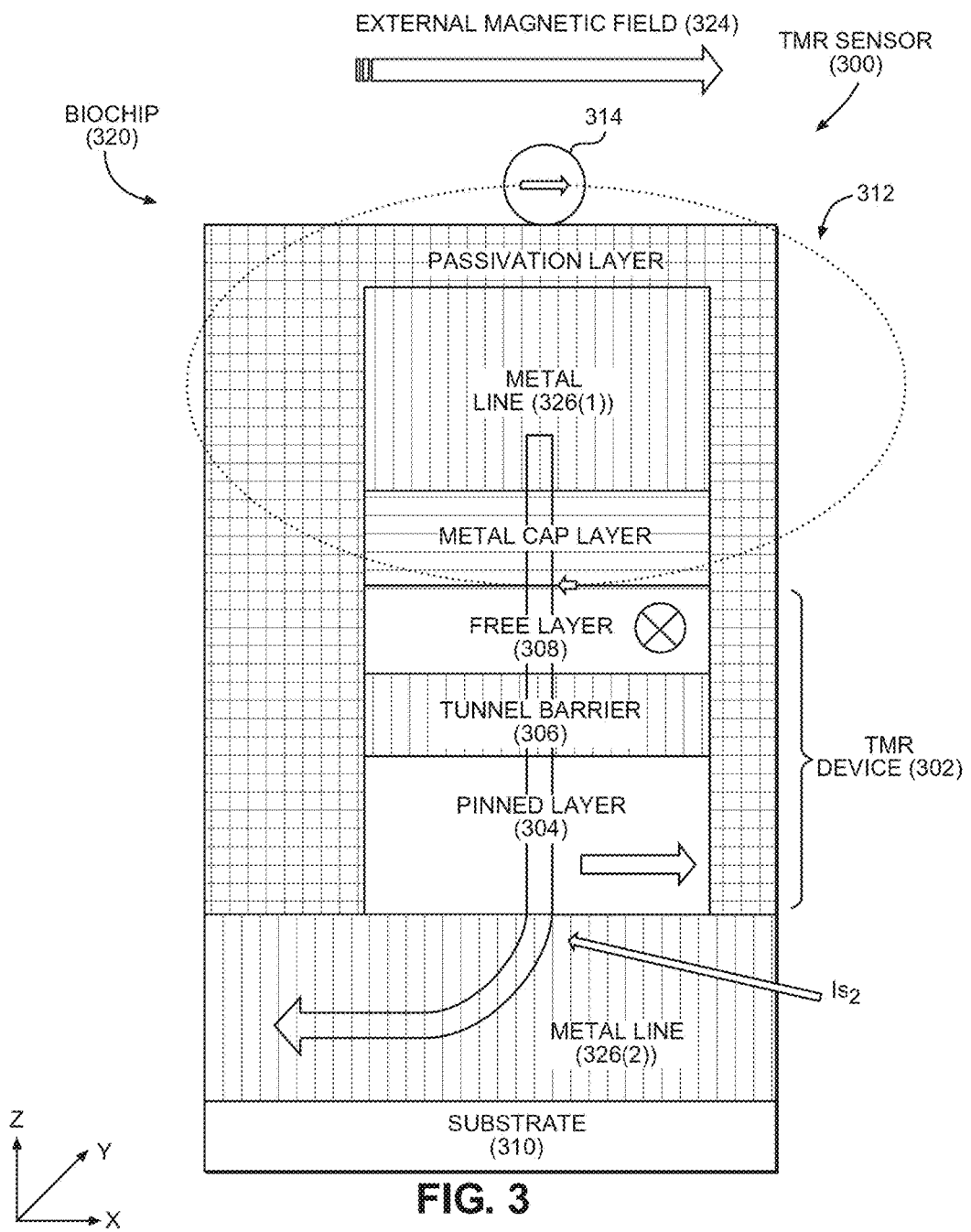
FIG. 3 is a schematic diagram of a tunnel magnetoresistive (TMR) sensor, that may be used as a biosensor, employing a TMR device in a chip whose resistance is configured to change in response to the presence of magnetic nanoparticles, which may be bound to a bioreceptor that is bound to a target analyte of interest, based on a TMR effect.
Figure 4:
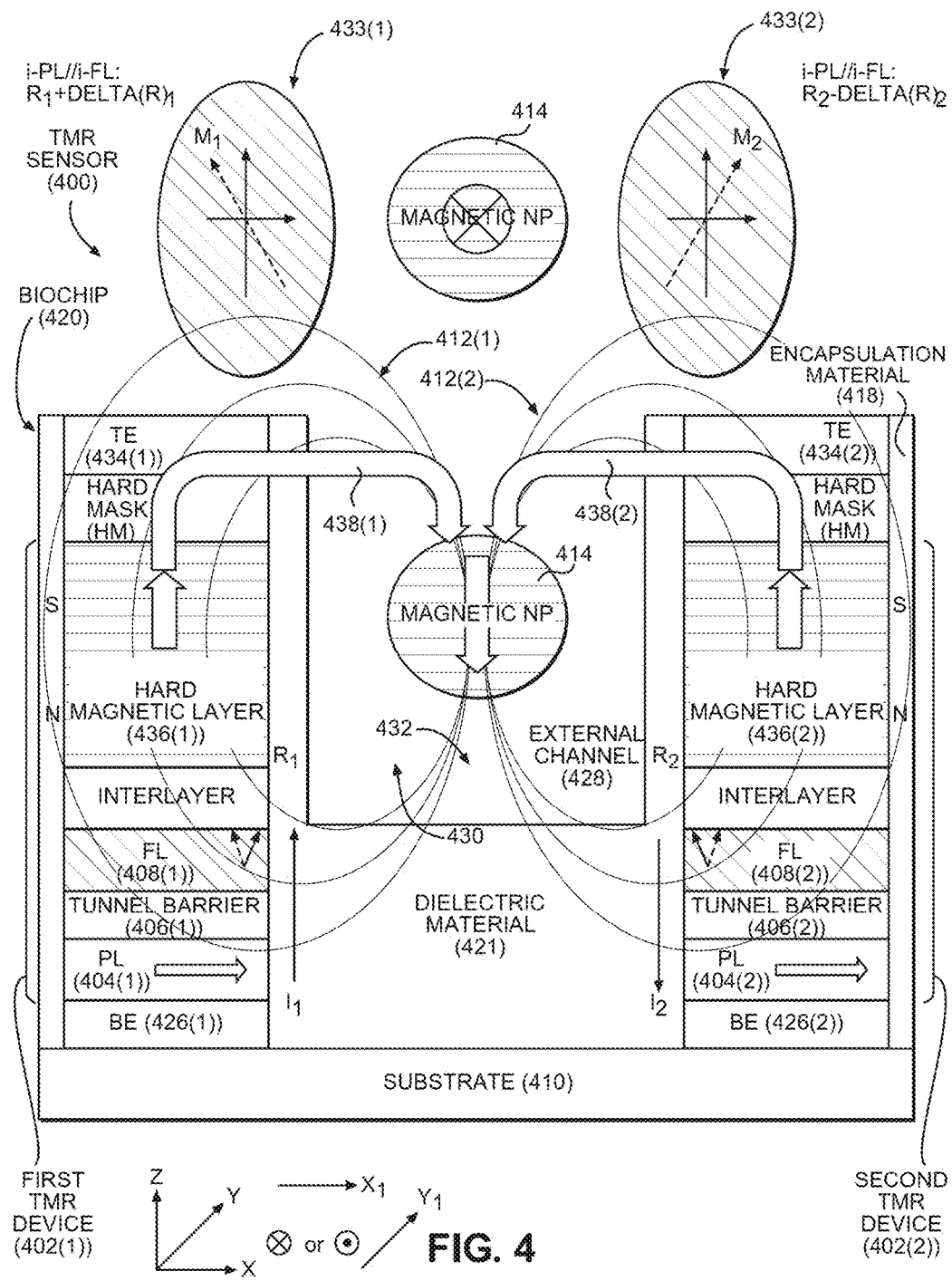
FIG. 4 is a schematic diagram of a TMR sensor employing dual TMR devices configured to provide differential magnetoresistive (MR) sensing of resistance change in response to the presence of magnetic nanoparticles, which may be bound to a bioreceptor that is bound to a target analyte of interest, in a channel disposed between the TMR devices, based on a TMR effect.

Before discussing MR sensor devices employing dual or multiple MR devices for differential MR sensing starting at FIG. 4, a TMR biosensor that can be used as a biosensor is discussed with regard to FIG. 3.

In this regard, FIG. 3 illustrates a TMR sensor 300 that can be used as a biosensor to detect the presence of magnetic nanoparticles bound to a bioreceptor bound to a target analyte of interest. The TMR sensor 300 can be fabricated using standard complementary metal-oxide semiconductor (CMOS) fabrication technology. The TMR effect of the TMR sensor 300 originates from its ability to tunnel current to flow between two (2) ferromagnetic layers. The magnitude of the resistance of the TMR sensor 300 is dependent on the angle of magnetization between the two (2) ferromagnetic layers. In this regard, the TMR sensor 300 includes a TMR device 302 that includes a pinned layer 304, a tunnel barrier 306, and a free layer 308 that has a fixed magnetization. The pinned layer 304 is formed on a substrate 310 and is a metal material (e.g., a Cobalt (Co) material) that has a fixed horizontal magnetization in the X direction, which is in-plane to the TMR device 302. The tunnel barrier 306, comprised of an insulating material metal spacer, is disposed above the pinned layer 304. The free layer 308 is disposed above the tunnel barrier 306. The magnetization of the free layer 308, which has an orthogonal alignment with the magnetization of the pinned layer 304, is configured to rotate based on the magnetic stray field 312 applied by the magnetic nanoparticles 314 to the free layer 308. The magnetic stray field 312 is provided by the magnetization of magnetic nanoparticles 314 captured by bioreceptors bound to a target analyte to be detected disposed external to the TMR sensor 300 such that the magnetic stray field 312 will interact with the free layer 308. For example, the magnetic nanoparticles 314 may be in a fluid form. Thus, the TMR sensor 300 may be provided as a biochip 320.

Figure 2:
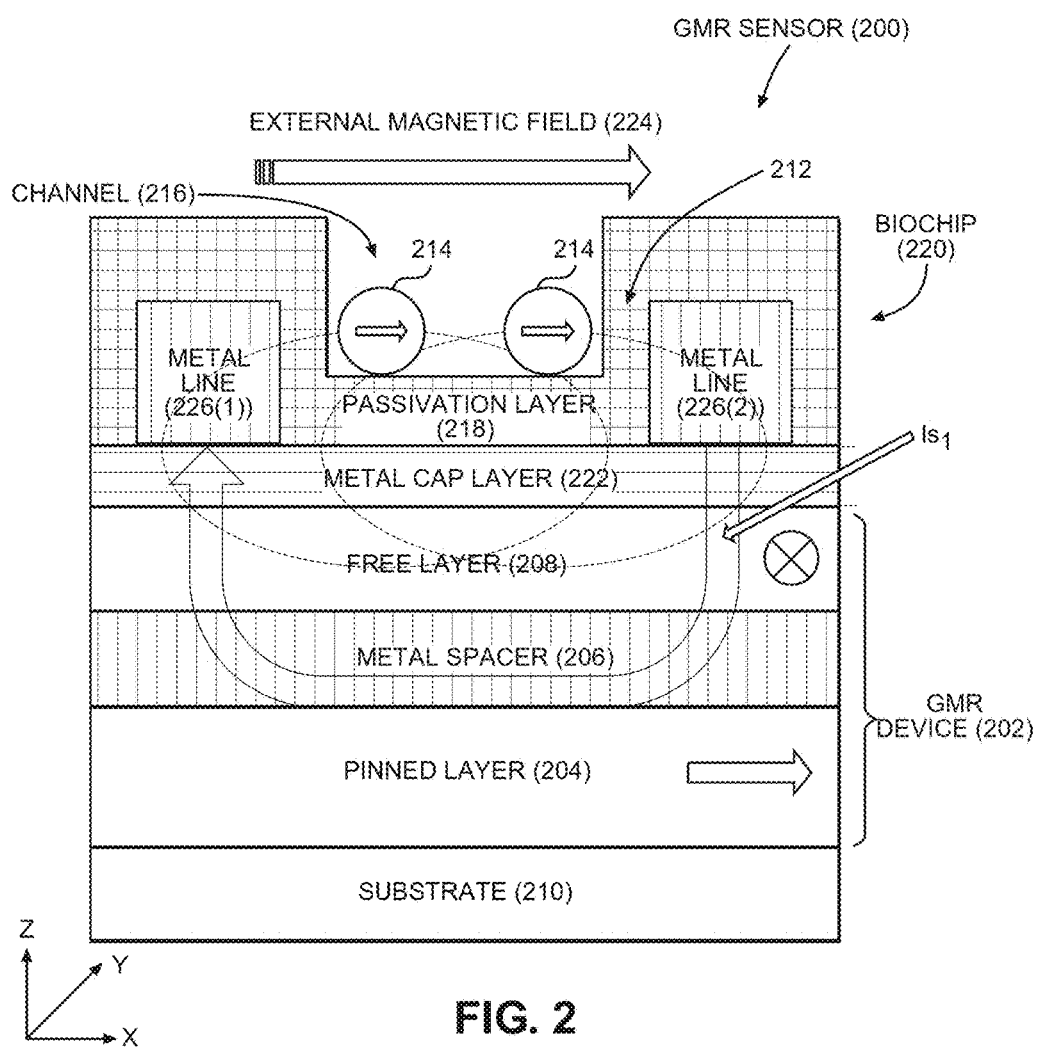
FIG. 2 is a schematic diagram of a giant magnetoresistive (GMR) sensor employing a GMR device in a chip whose resistance is configured to change in response to the presence of magnetic nanoparticles, which may be bound to a bioreceptor that is bound to a target analyte of interest, based on a GMR effect.

With continuing reference to FIG. 3, an external magnetic field 324, such as from an external coil, is applied to align the magnetic moments of the magnetic nanoparticles 314. The external magnetic field 324 may also saturate the magnetic moments of the magnetic nanoparticles 314. Thus, when the magnetic nanoparticles 314 are disposed above the free layer 308 of a first polarity, the magnetic stray field 312 of the magnetic nanoparticles 314 induces a magnetic moment change in the free layer 308 causing an angle variation of its magnetization state from an orthogonal magnetization state. This angle variation of magnetization between the free layer 308 and the pinned layer 304 creates a change in resistance of the TMR device 302 as compared to the orthogonal magnetization state of the free layer 308. For example, the magnetic stray field 312 may only disturb the magnetic moment of the free layer 308 such that the magnetic moment rotates in as little as one (1) degree for example. This change in resistance resulting from disturbing the magnetic moment of the free layer 308 can be determined based on sensing a voltage change in the TMR device 302. For example, a sense current $Is_e$ can be directed to flow through the TMR device 302 between metal lines 326(1), 326(2) to measure the voltage across the metal lines 326(1), 326(2) based on the resistance of the TMR device 302 according to Ohm's law. The TMR sensor 300 in FIG. 3 has advantages over the GMR sensor 200 in FIG. 2. The TMR sensor 300 has a higher MR ratio than the GMR sensor 200 in FIG. 2 to provide for a higher sensitivity of detecting the presence of the magnetic nanoparticles 314. For example, the MR ratio of the TMR device 302 may be between 100-300%, thereby providing a higher signal-to-noise ratio (SNR) of resistance change between the presence and lack of presence of the magnetic nanoparticles 314 resulting in a higher sensitivity device. Also, because the metal lines 326(1), 326(2) are not disposed adjacent to each other in the horizontal X direction, metal pitch is not an issue when scaling down the size of the TMR sensor 300. However, the external magnetic field 324 is also required beyond the biochip 320. Also, the magnetic nanoparticles 314 are separated a greater distance from the free layer 308 than separated in the GMR sensor 200 in FIG. 2 due to the current-perpendicular in-plane (CPP) design of the TMR sensor 300, thereby effectively reducing the improved SNR of the TMR sensor 300.

To further improve the SNR of a TMR sensor, which may be used as a biosensor, FIG. 4 illustrates a TMR sensor 400 that employs dual, first and second TMR devices 402(1), 402(2) that are MR devices. Note however, that more than two TMR devices 402 could be provided. The TMR sensor 400 may be provided in an integrated circuit (IC) biosensor chip 420. As will be discussed in more detail below, the first and second TMR devices 402(1), 402(2) are configured to provide differential MR sensing of resistance change in response to the presence of magnetic nanoparticles 414, which may be bound to a bioreceptor that is bound to a target analyte of interest, in an external channel 428 disposed between the TMR devices 402(1), 402(2). The external channel 428 is formed in a void 430 in an encapsulation material 418 such that the external channel 428 can capture magnetic nanoparticles 414 without the magnetic nanoparticles 414 physically contacting the internal components of the first and second TMR devices 402(1), 402(2). The first and second TMR devices 402(1), 402(2) are disposed on a substrate 410 and are disposed in the encapsulation material 418, which may include a dielectric material 421, formed above the substrate 410. The X, Y, and Z coordinates of the first and second TMR devices 402(1), 402(2) are shown in FIG. 4. The X and Y coordinates are in-plane to the first and second TMR devices 402(1), 402(2). The Z coordinate is out-of-plane to the first and second TMR devices 402(1), 402(2).

The first and second TMR devices 402(1), 402(2) each have first and second resistances $R_1$, $R_2$, respectively, based on their layer stackup of the first TMR device 402(1). In this regard, the first TMR device 402(1) has a first pinned layer (PL) 404(1) having a first magnetization in a first direction $X_1$. The first pinned layer 404(1) is disposed above and in electrical contact with a first bottom electrode (BE) 426(1). A first spacer comprised of a first tunnel barrier 406(1) made from an insulating material (e.g., Aluminum Oxide (AlOx) or Magnesium Oxide (MgO)) is disposed above the first pinned layer 404(1). A first free layer (FL) 408(1) is disposed above the first tunnel barrier 406(1) having a first magnetization in a second direction $Y_1$ in-plane to the GMR device 202 and orthogonal to the first direction $X_1$. Thus, the first tunnel barrier 406(1) forms a magnetic tunnel junction (MTJ). The magnetic moment of the first free layer 408(1) is configured to rotate from the second direction $Y_1$ towards the first direction $X_1$ in response to the presence of the magnetic nanoparticles 414 in the external channel 428 exerting a magnetic stray field 412(1) on the first free layer 408(1). A bottom surface 432 of the external channel 428 is disposed in a horizontal plane adjacent to the first TMR device 402(1) so that magnetic stray field 412(1) generated by the magnetic nanoparticles 414 reaches the first free layer 408(1), thereby causing the magnetic moment of the first free layer 408(1) to rotate. This rotation of the magnetic moment of the first free layer 408(1) causes the magnetization of the first free layer 408(1) to change with respect to the magnetization of the first pinned layer 404(1). In response, the first resistance $R_1$ of the first TMR device 402(1) increases as a result of exerting the magnetic stray field 412(1) on the first free layer 408(1).

Similarly, with continuing reference to FIG. 4, the second TMR device 402(2) has a second pinned layer 404(2) having a first magnetization in the first direction $X_1$. The second pinned layer 404(2) is disposed above and in electrical contact with a second bottom electrode 426(2). A first spacer comprised of a second tunnel barrier 406(2) made from an insulating material (e.g., Aluminum Oxide (AlOx) or Magnesium Oxide (MgO)) is disposed above the second pinned layer 404(2). A second free layer 408(2) is disposed above the second tunnel barrier 406(2) having the second magnetization in the second direction $Y_1$ orthogonal to the first direction $X_1$. Thus, the second tunnel barrier 406(2) forms an MTJ. The magnetic moment of the second free layer 408(2) is configured to rotate from the second direction $Y_1$ towards the first direction $X_1$ opposite from the rotation of the first free layer 408(1) in response to the presence of the magnetic nanoparticles 414 in the external channel 428 exerting a magnetic stray field 412(2) on the second free layer 408(2). This rotation of the magnetic moment of the second free layer 408(2) causes the magnetization of the second free layer 408(2) to change with respect to the magnetization of the second pinned layer 404(2). In response, the second resistance $R_2$ of the second TMR device 402(2) decreases.

Note that the first and second TMR devices 402(1), 402(2) could alternatively be fabricated such that their first and second free layers 408(1), 408(2) are disposed below the first and second tunnel barriers 406(1), 406(2), and their first and second pinned layers 404(1), 404(2) are disposed above the first and second tunnel barriers 406(1), 406(2).

The first and second TMR devices 402(1), 402(2) in the TMR sensor 400 in FIG. 4 can provide differential sensing of the magnetic nanoparticles 414 to improve the SNR of the TMR sensor 400, because the first and second resistances $R_1$, $R_2$ of the first and second TMR devices 402(1), 402(2) are arranged such that the first and second resistances $R_1$, $R_2$ change in opposite manners in response to the presence of the magnetic nanoparticles 414. For example, in the TMR sensor 400 in FIG. 4, the first resistance $R_1$ of the first TMR device 402(1) is configured to increase by a certain first delta resistance DELTA$(R)_1$ (e.g., in the range of micro-Ohms or nano-Ohms) as shown in top-view magnetization diagram 433(1) as the orthogonal magnetization state of the first free layer 408(1) changes to the $M_1$ magnetization state. The second resistance $R_2$ of the second TMR device 402(2) is configured to decrease by a certain second delta resistance DELTA$(R)_2$ (e.g., in the range of micro-Ohms or nano-Ohms), as shown in top-view magnetization diagram 433(2) as the orthogonal magnetization state of the second free layer 408(2) changes to the $M_2$ magnetization state. The first delta resistance DELTA$(R)_1$ and the second delta resistance DELTA$(R)_2$ may be approximately equal. Further, the first and second resistances $R_1$, $R_2$ may be approximately equal.

FIGS. 5A and 5B are diagrams illustrating exemplary magnetization diagrams 500, 502 of a free layer 408 in either the first or second TMR device 402(1), 402(2) in FIG. 4 when a magnetic stray field 412(1), 412(2) is not present from magnetic nanoparticles (MNP) 414 and when the magnetic stray field 412(1), 412(2) is generated in the presence of magnetic nanoparticles 414, respectively. As shown in FIG. 5A, the magnetic moment of the free layer 408 can rotate in the presence of a magnetic field, which is plotted in a theoretical graph 600 in FIG. 6A for different magnetic moment orientations 0, 1, 2, 3 corresponding to resistances 1.0, 2.0, 3.0. In the presence of the magnetic stray field 412(1), 412(2) from the magnetic nanoparticles 414, the magnetization of the free layer 408 is shown as rotating into different magnetic moment orientations 0, 1, 2, 3 which is plotted in a graph 602 in FIG. 6B for the different magnetic moment orientations 1, 2, 3, corresponding to resistances 0.9, 1.8, 2.7. The resistances in the graph 602 for magnetic moment orientations 1, 2, 3 differ from those in the graph 600, because of fabrication and other variations that may be present in the TMR devices 402(1), 402(2). Thus, the TMR devices' 402(1), 402(2) sensitivity to magnetic fields may be tested so that the first and second resistances $R_1$, $R_2$ can be calibrated to compensate for such variations and to equalize the changes in the first and second resistances $R_1$, $R_2$ in response to the presence of the magnetic nanoparticles 414.

With reference back to FIG. 4, the first and second TMR devices 402(1), 402(2) are disposed between and in electrical contact with respective bottom and top electrodes. In this regard, the first bottom electrode 426(1) is disposed below and in electrical contact with the first TMR device 402(1), and the first pinned layer 404(1) in this example. A first top electrode (TE) 434(1) is disposed above and also in electrical contact with the first TMR device 402(1), and the first free layer 408(1) in this example. Thus, the first TMR device 402(1) is configured to carry a first current $I_1$ between the first bottom electrode 426(1) and the first top electrode 434(1) in response to a first voltage differential applied between the first bottom electrode 426(1) and the first top electrode 434(1) based on the first resistance $R_1$ of the first TMR device 402(1). The second bottom electrode 426(2) is disposed below and in electrical contact with the second TMR device 402(2), and the second pinned layer 404(2) in this example. A second top electrode 434(2) is disposed above and also in electrical contact with the second TMR device 402(2), and the second free layer 408(2) in this example. The second TMR device 402(2) is configured to carry a second current $I_2$ between the second bottom electrode 426(2) and the second top electrode 434(2) in response to a second voltage differential applied between the second bottom electrode 426(2) and the second top electrode 434(2) based on the second resistance $R_2$ of the second TMR device 402(2). As will be discussed below, these currents $I_1$, $I_2$ can be sensed to generate differential signals indicative of the differential change in resistances $R_1$, $R_2$ in the first and second TMR devices 402(1), 402(2) in response to the magnetic nanoparticles 414.

To provide for the ability to generate a magnetic bias field in the external channel 428 to align the magnetic moment of the magnetic nanoparticles 414, the first and second TMR devices 402(1), 402(2) in this example also include first and second hard magnetic layers 436(1), 436(2). For example, the first and second hard magnetic layers 436(1), 436(2) may have perpendicular magnetizations as shown in FIG. 4. The first and second hard magnetic layers 436(1), 436(2) are configured to generate first and second magnetic bias fields 438(1), 438(2), respectively in the external channel 428 to align the magnetic moment of magnetic nanoparticles 414 disposed in the external channel 428. The first and second hard magnetic layers 436(1), 436(2) may also be configured to generate the first and second magnetic bias fields 438(1), 438(2) to saturate magnetic moments of the magnetic nanoparticles 414. For example, the first and second hard magnetic layers 436(1), 436(2) may be made from a metal material, such as Cobalt (Co), Platinum (Pt), Palladium (Pd), Iron (Fe), Chromium (Cr), CoPt, multiple alternative layers of CoPt ("CoPt multi-layer"), CoPd, Co Nickel (Ni) (CoNi), Terbium (Tb) Co (TbCo), TbFeCo, FePt, and CoCrPt, as non-limiting examples. In this manner, an external magnetic field generator, such as a coil for example, is not required to be provided to generate a magnetic bias field in the external channel 428 to align the magnetic moment of magnetic nanoparticles 414 disposed in the external channel 428. Thus, the magnetic bias fields 438(1), 438(2) can be provided in the TMR sensor 400 on-chip, in the biochip 420 for example. In this example, the first hard magnetic layer 436(1) is configured to generate the first magnetic bias field 438(1) in the external channel 428 having a north (N) to south (S) direction. The second hard magnetic layer 436(2) is configured to generate the second magnetic bias field 438(2) in the external channel 428 in a north (N) to south (S) to north (N) direction.

Also, as another example with reference to the TMR sensor 400 in FIG. 4, by providing the external channel 428 between the first and second TMR devices 402(1), 402(2), the magnetic stray fields 412(1), 412(2) generated by the magnetic nanoparticles 414 can more easily rotate the magnetic moment orientations (i.e., magnetization) of the free layers 408(1), 408(2) in the first and second TMR devices 402(1), 402(2) for a given stray magnetic strength. This is due to reduced distance between the free layers 408(1), 408(2) and the magnetic nanoparticles 414 when disposed in the external channel 428, thereby further increasing the signal-to-noise ratio (SNR) of the TMR sensor 400.

The TMR sensor 400 may enjoy other advantages. For example, the MR ratio of the TMR devices 402(1), 402(2) may be between 60%-500%, and typically between 100%-300% to provide a higher SNR. Coupled with the differential MR sensing, the SNR is further increased. The size of the first and second TMR devices 402(1), 402(2) may be scalable down to nanometers (nm) (e.g., 40-100 nm), because a metal pitch does not have to be maintained between the first and second bottom electrodes 426(1), 426(2) and their respective first and second top electrodes 434(1), 434(2). The resistance of the first and second TMR devices 402(1), 402(2) is dominated by their junction sizes and their first and second tunnel barriers 406(1), 406(2). Sizing of the TMR sensor 400 may be important depending on the application, such as for a wearable or point-of-care device. For example, the sensitivity of the TMR sensor 400 may need to be designed to be different for a wearable or point-of-care device. The application and fabrication temperature of the first and second TMR devices 402(1), 402(2) may be able to be increased to higher temperatures (e.g., 300-400 Celsius), because the first and second tunnel barriers 406(1), 406(2) are made from non-metallic insulating materials that will not diffuse before 400 Celsius for example.

Figure 7:
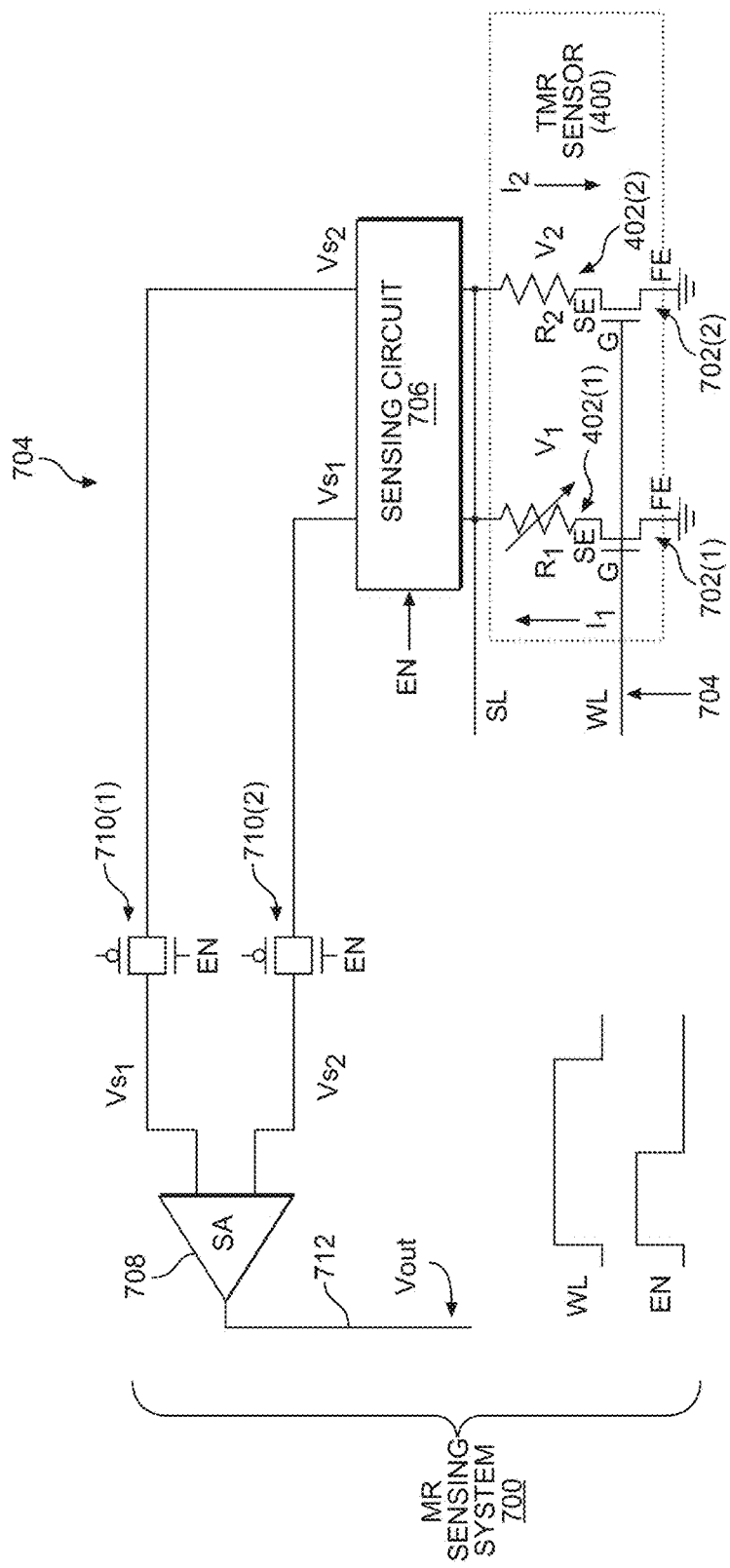
FIG. 7 is a schematic diagram of an exemplary MR sensing system employing the TMR sensor in FIG. 4, a sensing circuit configured to generate differential voltage signals based on the sensed differential change in resistance between the TMR devices in the TMR sensor in the presence of magnetic nanoparticles, and a sense amplifier configured to amplify the differential voltage signals.
Figure 8:
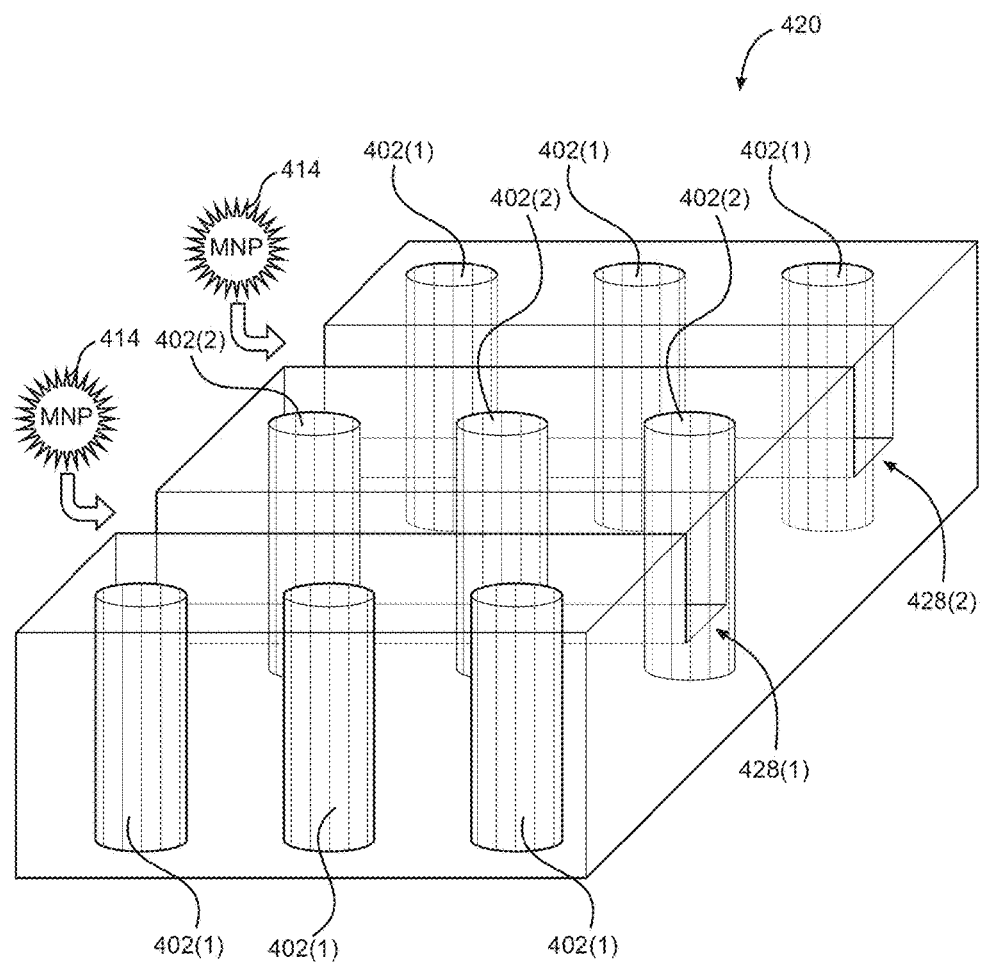
FIG. 8 is a schematic diagram of an exemplary biosensor chip employing a plurality of MR sensors in FIG. 4 for detecting magnetic nanoparticles, and which may also employ the MR sensing system in FIG. 7.

FIG. 7 is a schematic diagram of an exemplary MR sensing system 700 that can employ the TMR sensor 400 in FIG. 4 generating differential signals representing the detection of magnetic nanoparticles 414 based on the differential change in resistances $R_1$, $R_2$ of the TMR sensor 400. In this regard, the first and second TMR devices 402(1), 402(2) of the TMR sensor 400 are represented in circuit form as resistances $R_1$, $R_2$. First and second access transistors 702(1), 702(2) are provided in the TMR sensor 400 to activate a TMR device 402(1), 402(2). Note that the MR sensing system 700 may have a plurality of TMR sensors 400 like shown in the biosensor chip 420 in FIG. 8, but only one (1) is shown in this example. Each of the first and second access transistors 702(1), 702(2) includes a gate (G), a first electrode (FE), and a second electrode (SE). The gates (G) are coupled to a word line (WL). The first electrodes (FE) are coupled to the first and second bottom electrodes 426(1), 426(2) of the first and second TMR devices 402(1), 402(2) (see also FIG. 4). The first and second top electrodes 434(1), 434(2) of the first and second TMR devices 402(1), 402(2) (see FIG. 4) are coupled to a selector line (SL). The first and second TMR devices 402(1), 402(2) are each configured to receive first and second currents $I_1$, $I_2$ (see FIG. 4) between their first and second top electrodes 434(1), 434(2) and their respective first and second bottom electrode 426(1), 426(2) based on the first and second resistances $R_1$, $R_2$ of the first and second TMR devices 402(1), 402(2), in response to a control signal 704 on the word line (WL) activating the first and second access transistors 702(1), 702(2) and a voltage $V_1$, $V_2$ applied to the selector line (SL).

With continuing reference to FIG. 7, a sensing circuit 706 is provided in the MR sensing system 700. The sensing circuit 706 is configured to receive the first and second currents $I_1$, $I_2$ from the first and second TMR devices 402(1), 402(2) of the TMR sensor 400 in response to an enable signal EN indicating an enable state (high state in this example). In response to the enable signal EN indicating the enable state, the sensing circuit 706 is configured to receive the first current L from the first TMR device 402(1), and the second current $I_2$ from the second TMR device 402(2). The sensing circuit 706 is configured to generate a first sensed voltage $Vs_1$ and a second sensed voltage $Vs_2$ indicative of the sensed first and second currents $I_1$, $I_2$ representing the first and second resistances $R_1$, $R_2$ of the first and second TMR devices 402(1), 402(2). For example, the sensing circuit 706 may be a current-latched sense amplifier (CLSA). For example, the sensing circuit 706 may be the N-type (N) MOS offset-cancelling (OC) current-latched (CL) sense amplifier (SA) (NOC-CLSA) as described in Kim et al., "*A 45 nm 1 Mb Embedded STT-MRAM with design techniques to minimize read-disturbance,*" which is incorporated by reference herein in its entirety.

With continuing reference to FIG. 7, a sense amplifier (SA) 708 is also provided in the MR sensing system 700. The sense amplifier 708 is configured to receive the first and second sensed voltages $Vs_1$ and $Vs_2$ from the sensing circuit 706. In this example, a first input circuit 710(1) and a second input circuit 710(2) provided in the form of pass gates control the timing of the sense amplifier 708 receiving the first and second sensed voltages $Vs_1$ and $Vs_2$ from the sensing circuit 706 based on the enable signal EN. The first input circuit 710(1) is configured to pass the first sensed voltage $Vs_1$, and the second input circuit 710(2) is configured to pass the second sensed voltage $Vs_2$ during the second sensing phase SS2. The sense amplifier 708 is configured to sense the first sensed voltage $Vs_1$ and the second sensed voltage $Vs_2$ based on the differential voltage therebetween to generate an amplified differential output voltage Vout on an output node 712 indicative of the resistance state of the TMR devices 402(1), 402(2).

Figure 9:
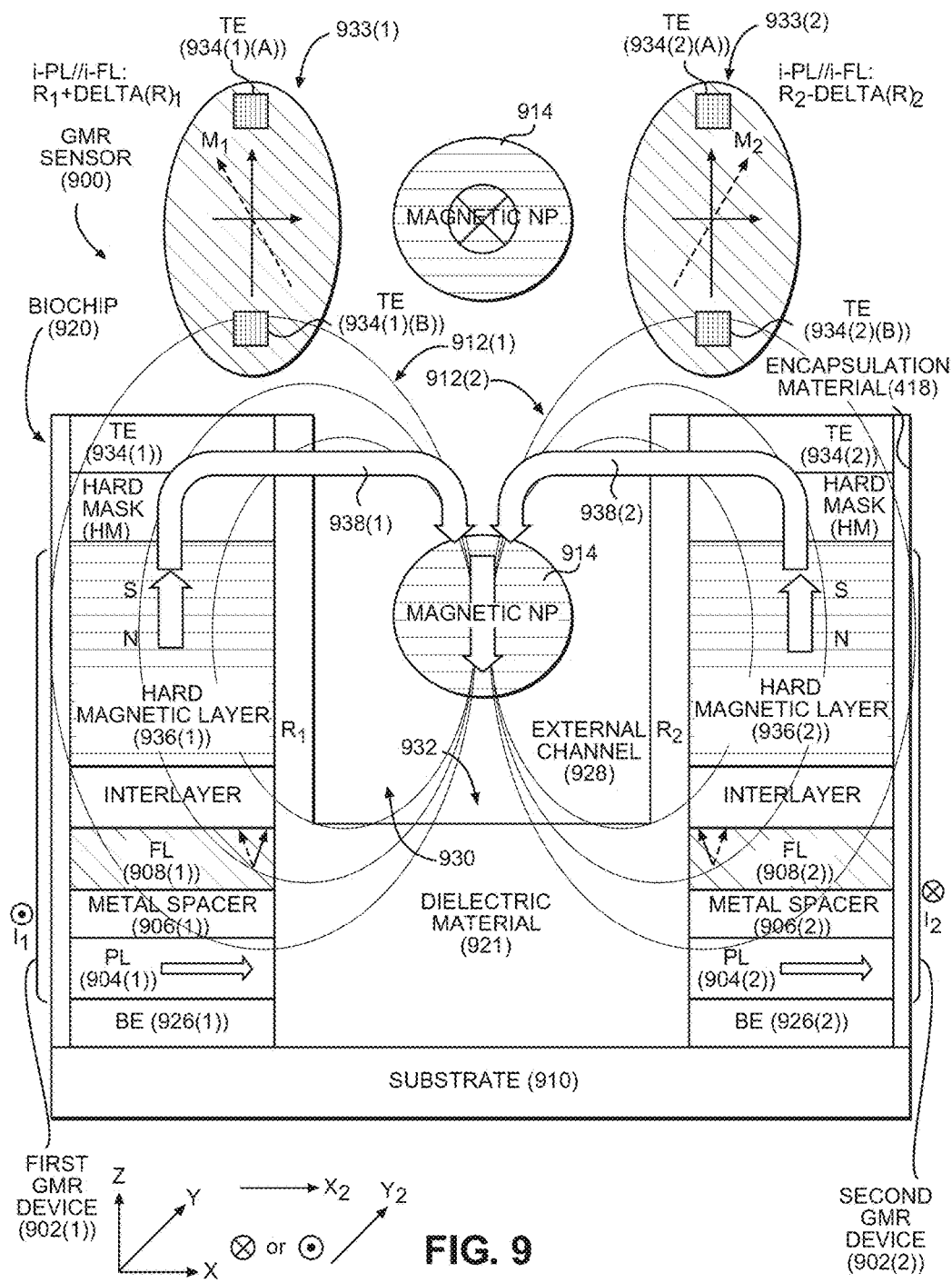
FIG. 9 is a schematic diagram of an exemplary GMR sensor employing dual GMR devices configured to provide differential MR sensing of resistance change in response to the presence of magnetic nanoparticles, which may be bound to a bioreceptor that is bound to a target analyte of interest, in a channel disposed between the GMR devices, based on a GMR effect.

Dual or multiple GMR devices could also be employed in a MR sensor for differential MR sensing to improve SNR of a GMR sensor, which may be used as a biosensor. In this regard, FIG. 9 illustrates a GMR sensor 900 that employs dual, first and second GMR devices 902(1), 902(2) that are MR devices. The GMR sensor 900 may be provided in an IC biosensor chip 920. As will be discussed in more detail below, the first and second GMR devices 902(1), 902(2) are configured to provide differential GMR sensing of resistance change in response to the presence of magnetic nanoparticles 914, which may be bound to a bioreceptor that is bound to a target analyte of interest, in an external channel 928 disposed between the GMR devices 902(1), 902(2). The external channel 928 is formed in a void 930 in an encapsulation material 918 such that the external channel 928 can capture magnetic nanoparticles 914 without the magnetic nanoparticles 914 physically contacting the internal components of the first and second GMR devices 902(1), 902(2). The first and second GMR devices 902(1), 902(2) are disposed on a substrate 910 and disposed in the encapsulation material 918 which may include a dielectric material 921, formed above the substrate 910. The X, Y, and Z coordinates of the first and second GMR devices 902(1), 902(2) are shown in FIG. 9. The X and Y coordinates are in-plane to the first and second GMR devices 902(1), 902(2). The Z coordinate is out-of-plane to the first and second GMR devices 902(1), 902(2).

The first and second GMR devices 902(1), 902(2) each have first and second resistances $R_1$, $R_2$, respectively, based on their layer stackup of the first GMR device 902(1). In this regard, the first GMR device 902(1) has a first pinned layer 904(1) having a first magnetization in a first direction $X_2$. The first pinned layer 904(1) is disposed above and in electrical contact with a first bottom electrode 926(1). A first spacer comprised of a first metal spacer 906(1) is made from a metal material disposed above the first pinned layer 904(1). A first free layer 908(1) having a first magnetization in a second direction $Y_2$ orthogonal to the first direction $X_2$ is disposed above the first metal spacer 906(1). Thus, the first metal spacer 906(1) forms a GMR junction. The magnetic moment of the first free layer 908(1) is configured to rotate from the second direction $Y_2$ towards the first direction $X_2$ in response to the presence of the magnetic nanoparticles 914 in the external channel 928 exerting a magnetic stray field 912(1) on the first free layer 908(1). A bottom surface 932 of the external channel 928 is disposed in a horizontal plane adjacent to the first GMR device 902(1) so that the magnetic stray field 912(1) generated by the magnetic nanoparticles 914 reaches the first free layer 908(1), thereby causing the magnetic moment of the first free layer 908(1) to rotate. This rotation of the magnetic moment of the first free layer 908(1) causes the magnetization of the first free layer 908(1) to change with respect to the magnetization of the first pinned layer 904(1). In response, first resistance $R_1$ of the first GMR device 902(1) increases as a result of exerting the magnetic stray field 912(1) on the first free layer 908(1).

Similarly, with continuing reference to FIG. 9, the second GMR device 902(2) has a second pinned layer 904(2) having a first magnetization in the first direction $X_2$. The second pinned layer 904(2) is disposed above and in electrical contact with a second bottom electrode 926(2). A second metal spacer 906(2) comprised of a metal material is disposed above the second pinned layer 904(2). A second free layer 908(2) having the second magnetization in the second direction $Y_2$ orthogonal to the first direction $X_2$ is disposed above the second metal spacer 906(2). Thus, the second metal spacer 906(2) forms a GMR junction. The magnetic moment of the second free layer 908(2) is configured to rotate from the second direction $Y_2$ towards the first direction $X_2$ opposite from the rotation of the first free layer 908(1) in response to the presence of the magnetic nanoparticles 914 in the external channel 928 exerting a magnetic stray field 912(2) on the second free layer 908(2). This rotation of the magnetic moment of the second free layer 908(2) causes the magnetization of the second free layer 908(2) to change with respect to the magnetization of the second pinned layer 904(2). In response, the second resistance $R_2$ of the second GMR device 902(2) decreases as a result of exerting the magnetic stray field 912(1) on the second free layer 908(2).

Note that the first and second GMR devices 902(1), 902(2) could alternatively be fabricated such that their first and second free layers 908(1), 908(2) are disposed below the first and second metal spacers 906(1), 906(2), and their first and second pinned layers 904(1), 904(2) are disposed above the first and second metal spacers 906(1), 906(2).

The first and second GMR devices 902(1), 902(2) in the GMR sensor 900 in FIG. 9 can provide differential sensing of the magnetic nanoparticles 914 to improve the SNR of the GMR sensor 900, because the first and second resistances $R_1$, $R_2$ of the first and second GMR devices 902(1), 902(2) are arranged such that the first and second resistances $R_1$, $R_2$ change in opposite manners in response to the presence of the magnetic nanoparticles 914. For example, in the GMR sensor 900 in FIG. 9, the first resistance $R_1$ of the first GMR device 902(1) is configured to increase by a certain first delta resistance $DELTA(R)_1$ (e.g., in the range of micro-Ohms or nano-Ohms) as shown in top-view magnetization diagram 933(1) as the orthogonal magnetization state of the first free layer 908(1) changes to the $M_1$ magnetization state. The second resistance $R_2$ of the second GMR device 902(2) is configured to increase by a certain second delta resistance $DELTA(R)_2$, as shown in top-view magnetization diagram 933(1) as the orthogonal magnetization state of the second free layer 908(2) changes to the $M_2$ magnetization state. The first delta resistance $DELTA(R)_1$ and the second delta resistance $DELTA(R)_2$ may be approximately equal. Further, the first and second resistances $R_1$, $R_2$ may be approximately equal.

With continuing reference to FIG. 9, the first and second GMR devices 902(1), 902(2) are disposed between and in electrical contact with respective bottom and top electrodes. In this regard, the first bottom electrode 926(1) is disposed below and in electrical contact with the first GMR device 902(1), and the first pinned layer 904(1) in this example. Two (2) first top electrodes 934(1)(A), 934(1)(B) are disposed above and also in electrical contact with the first GMR device 902(1), and the first free layer 908(1) in this example.

Thus, the first GMR device 902(1) is configured to carry a first current $I_1$ flowing in-plane in FIG. 9 in response to a first voltage differential applied between the two (2) top electrodes 934(1)(A), 934(1)(B) based on the first resistance $R_1$ of the first GMR device 902(1). The second bottom electrode 926(2) is disposed below and in electrical contact with the second GMR device 902(2), and the second pinned layer 904(2) in this example. Two (2) second top electrodes 934(2)(A), 934(2)(B) are disposed above and also in electrical contact with the second GMR device 902(2), and the second free layer 908(2) in this example. The second GMR device 902(2) is configured to carry a second current $I_2$ flowing in-plane in FIG. 9 between the two (2) second top electrodes 934(2)(A), 934(2)(B) in response to a second voltage differential applied between the two (2) second top electrodes 934(2)(A), 934(2)(B) based on the second resistance $R_2$ of the second GMR device 902(2). As will be discussed below, these currents $I_1$, $I_2$ can be sensed to generate differential signals indicative of the differential change in resistances $R_1$, $R_2$ in the first and second GMR devices 902(1), 902(2) in response to the magnetic nanoparticles 914.

To provide for the ability to generate a magnetic bias field in the external channel 928 to align the magnetic moment of the magnetic nanoparticles 914, the first and second GMR devices 902(1), 902(2) in this example also include first and second hard magnetic layers 936(1), 936(2). For example, the first and second hard magnetic layers 936(1), 936(2) may have perpendicular magnetizations as shown in FIG. 9. The first and second hard magnetic layers 936(1), 936(2) are configured to generate first and second magnetic bias fields 938(1), 938(2), respectively in the external channel 928 to align the magnetic moment of magnetic nanoparticles 914 disposed in the external channel 928. The first and second hard magnetic layers 936(1), 936(2) may also be configured to generate the first and second magnetic bias fields 938(1), 938(2) to saturate the magnetic moment of the magnetic nanoparticles 914 disposed in the external channel 928. For example, the first and second hard magnetic layers 936(1), 936(2) may be made from a metal material, such as Cobalt (Co), Platinum (Pt), Palladium (Pd), Iron (Fe), Chromium (Cr), CoPt, multiple alternative layers of CoPt ("CoPt multi-layer"), CoPd, Co Nickel (Ni) (CoNi), Terbium (Tb) Co (TbCo), TbFeCo, FePt, and CoCrPt, as non-limiting examples. In this manner, an external magnetic field generator, such as a coil for example, is not required to be provided to generate a magnetic bias field in the external channel 928 to align the magnetic moment of magnetic nanoparticles 914 disposed in the external channel 928. Thus, the magnetic bias fields 938(1), 938(2) can be provided in the GMR sensor 900 on-chip, in the biochip 920 for example. In this example, the first hard magnetic layer 936(1) is configured to generate the first magnetic bias field 938(1) in the external channel 928 having a north (N) to south (S) direction. The second hard magnetic layer 936(2) is configured to generate the second magnetic bias field 938(2) in the external channel 928 in a north (N) to south (S) to north direction.

Also, as another example with reference to the GMR sensor 900 in FIG. 9, by providing the external channel 928 between the first and second GMR devices 902(1), 902(2), the magnetic stray fields 912(1), 912(2) generated by the magnetic nanoparticles 914 can more easily rotate the magnetic moment orientations of the free layers 908(1), 908(2) in the first and second GMR devices 902(1), 902(2) for a given stray magnetic strength. This is due to reduced distance between the free layers 908(1), 908(2) and the magnetic nanoparticles 914 when disposed in the external channel 928, thereby further increasing the signal-to-noise ratio (SNR) of the GMR sensor 900.

Figure 10:
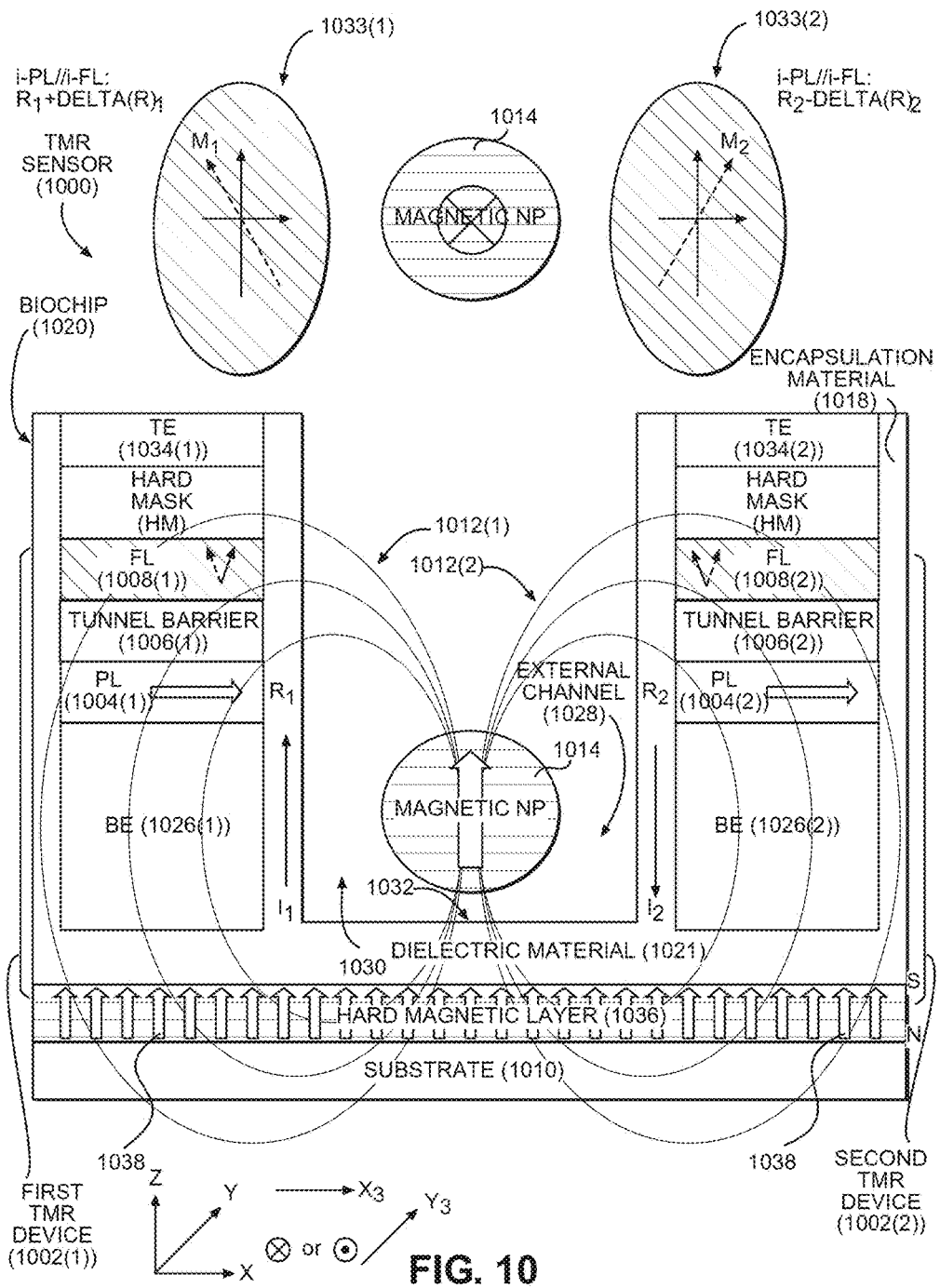
FIG. 10 is a schematic diagram of another exemplary TMR sensor employing dual TMR devices configured to provide differential MR sensing of resistance change in response to the presence of magnetic nanoparticles in a channel disposed between the TMR devices based on a TMR effect, and employing a hard magnetic layer disposed beneath the channel and outside of the TMR devices to generate a magnetic bias field in the channel to align magnetic moments of the magnetic nanoparticles disposed therein.

FIG. 10 is a schematic diagram of another exemplary TMR sensor 1000 employing dual TMR devices 1002(1), 1002(2) configured to provide differential MR sensing of resistance change in response to the presence of magnetic nanoparticles 1014 in an external channel 1028 similar to the TMR sensor 400 in FIG. 4. However, in this example, a hard magnetic layer 1036 is disposed beneath the external channel 1028 and outside of the TMR devices 1002(1), 1002(2) to generate a magnetic bias field 1038 in the external channel 1028 to align the magnetic moments of the magnetic nanoparticles 1014 disposed therein.

As shown in FIG. 10, the TMR sensor 1000 employs dual, first and second TMR devices 1002(1), 1002(2) that are MR devices. Note however, that more than two TMR devices 1002 could be provided. The TMR sensor 1000 may be provided in an IC biosensor chip 1020. As will be discussed in more detail below, the first and second TMR devices 1002(1), 1002(2) are configured to provide differential MR sensing of resistance change in response to the presence of magnetic nanoparticles 1014, which may be bound to a bioreceptor that is bound to a target analyte of interest, in the external channel 1028 disposed between the TMR devices 1002(1), 1002(2). The external channel 1028 is formed in a void 1030 in an encapsulation material 1018 such that the external channel 1028 can capture magnetic nanoparticles 1014 without the magnetic nanoparticles 1014 physically contacting the internal components of the first and second TMR devices 1002(1), 1002(2). The first and second TMR devices 1002(1), 1002(2) are disposed on a substrate 1010 and disposed in the encapsulation material 1018 which may include a dielectric material 1021, formed above the substrate 1010. The X, Y, and Z coordinates of the first and second TMR devices 1002(1), 1002(2) are shown in FIG. 10. The X and Y coordinates are in-plane to the first and second TMR devices 1002(1), 1002(2). The Z coordinate is out-of-plane to the first and second TMR devices 1002(1), 1002(2).

The first and second TMR devices 1002(1), 1002(2) each have first and second resistances $R_1$, $R_2$, respectively, based on their layer stackup of the first TMR device 1002(1). In this regard, the first TMR device 1002(1) has a first pinned layer 1004(1) having a first magnetization in a first direction $X_3$. The first pinned layer 1004(1) is disposed above and in electrical contact with a first bottom electrode 1026(1). A first spacer comprised of a first tunnel barrier 1006(1) made from an insulating material (e.g., Aluminum Oxide (AlOx) or Magnesium Oxide (MgO)) is disposed above the first pinned layer 1004(1). A first free layer 1008(1) is disposed above the first tunnel barrier 1006(1) having a first magnetization in a second direction $Y_3$ orthogonal to the first direction $X_3$. Thus, the first tunnel barrier 1006(1) forms an MTJ. The magnetic moment of the first free layer 1008(1) is configured to rotate from the second direction $Y_3$ towards the first direction $X_3$ in response to the presence of the magnetic nanoparticles 1014 in the external channel 1028 exerting a magnetic stray field 1012(1) on the first free layer 1008(1). A bottom surface 1032 of the external channel 1028 is disposed in a horizontal plane adjacent to the first TMR device 1002(1), 1002(2) so that the magnetic stray field 1012(1) generated by the magnetic nanoparticles 1014 reaches the first free layer 1008(1), thereby causing the magnetic moment of the first free layer 1008(1) to rotate. In response, first resistance $R_1$ of the first TMR device 1002(1) increases, exerting the magnetic stray field 1012(1) on the first free layer 1008(1). This rotation of the magnetic moment of the first free layer 1008(1) causes the magnetization of the first free layer 1008(1) to change with respect to the magnetization of the first pinned layer 1004(1). In response, the first resistance $R_1$ of the first TMR device 1002(1) increases as a result of exerting the magnetic stray field 1012(1) on the first free layer 1008(1). Note that in this example, the bottom surface 1032 of the external channel 1028 extends below the horizontal plane of the first free layer 1008(1).

Similarly, with continuing reference to FIG. 10, the second TMR device 1002(2) has a second pinned layer 1004(2) having a first magnetization in the first direction $X_3$. The second pinned layer 1004(2) is disposed above and in electrical contact with a second bottom electrode 1026(2). A first spacer comprised of a second tunnel barrier 1006(2) made from an insulating material (e.g., Aluminum Oxide (AlOx) or Magnesium Oxide (MgO)) is disposed above the second pinned layer 1004(2). A second free layer 1008(2) is disposed above the second tunnel barrier 1006(2) having the second magnetization in the second direction $Y_3$ orthogonal to the first direction $X_3$. Thus, the second tunnel barrier 1006(2) forms an MTJ. The magnetic moment of the second free layer 1008(2) is configured to rotate from the second direction $Y_3$ towards the first direction $X_3$ opposite from the rotation of the first free layer 1008(1) in response to the presence of the magnetic nanoparticles 1014 in the external channel 1028 exerting a magnetic stray field 1012(1) on the second free layer 1008(2). This rotation of the magnetic moment of the second free layer 1008(2) causes the magnetization of the second free layer 1008(2) to change with respect to the magnetization of the second pinned layer 1004(2). In response, the second resistance $R_2$ of the second TMR device 1002(2) decreases as a result of exerting the magnetic stray field 1012(1) on the second free layer 1008(2).

Note that the first and second TMR devices 1002(1), 1002(2) could alternatively be fabricated such that their first and second free layers 1008(1), 1008(2) are disposed below the first and second tunnel barriers 1006(1), 1006(2), and their first and second pinned layers 1004(1), 1004(2) are disposed above the first and second tunnel barriers 1006(1), 1006(2).

The first and second TMR devices 1002(1), 1002(2) in the TMR sensor 1000 in FIG. 10 can provide differential sensing of the magnetic nanoparticles 1014 to improve the SNR of the TMR sensor 1000, because the first and second resistances $R_1$, $R_2$ of the first and second TMR devices 1002(1), 1002(2) are arranged such that the first and second resistances $R_1$, $R_2$ change in opposite manners in response to the presence of the magnetic nanoparticles 1014. For example, in the TMR sensor 1000 in FIG. 10, the first resistance $R_1$ of the first TMR device 1002(1) is configured to increase by a certain first delta resistance DELTA($R$)$_1$ (e.g., in the range of micro-Ohms or nano-Ohms) as shown in a top-view magnetization diagram 1033(1) as the orthogonal magnetization state of the first free layer 1008(1) changes to the $M_1$ magnetization state. The second resistance $R_1$ of the second TMR device 1002(2) is configured to decrease by a certain second delta resistance DELTA($R$)$_2$ (e.g., in the range of micro-Ohms or nano-Ohms), as shown in a top-view magnetization diagram 1033(2) as the orthogonal magnetization state of the second free layer 1008(2) changes to the $M_2$ magnetization state. The first delta resistance DELTA($R$)$_1$ and the second delta resistance DELTA($R$)$_2$ may be approximately equal. Further, the first and second resistances $R_1$, $R_2$ may be approximately equal.

With continuing reference to FIG. 10, the first and second TMR devices 1002(1), 1002(2) are disposed between and in electrical contact with respective bottom and top electrodes. In this regard, the first bottom electrode 1026(1) is disposed below and in electrical contact with the first TMR device 1002(1), and the first pinned layer 1004(1) in this example. A first top electrode 1034(1) is disposed above and also in electrical contact with the first TMR device 1002(1), and the first free layer 1008(1) in this example. Thus, the first TMR device 1002(1) is configured to carry a first current $I_1$ between the first bottom electrode 1026(1) and the first top electrode 1034(1) in response to a first voltage differential applied between first bottom electrode 1026(1) and the first top electrode 1034(1) based on the first resistance $R_1$ of the first TMR device 1002(1). The second bottom electrode 1026(2) is disposed below and in electrical contact with the second TMR device 1002(2), and the second pinned layer 1004(2) in this example. A second top electrode 1034(2) is disposed above and also in electrical contact with the second TMR device 1002(2), and the second free layer 1008(2) in this example. The second TMR device 1002(2) is configured to carry a second current $I_2$ between the second bottom electrode 1026(2) and the second top electrode 1034(2) in response to a second voltage differential applied between the second bottom electrode 1026(2) and the second top electrode 1034(2) based on the second resistance $R_2$ of the second TMR device 1002(2). As will be discussed below, these currents $I_1$, $I_2$ can be sensed to generate differential signals indicative of the differential change in resistances $R_1$, $R_2$ in the first and second TMR devices 1002(1), 1002(2) in response to the magnetic nanoparticles 1014.

To provide for the ability to generate a magnetic bias field 1038 in the external channel 1028 to align the magnetic moment of the magnetic nanoparticles 1014, the hard magnetic layer 1036 is provided in the TMR sensor 1000. In this example, the hard magnetic layer 1036 is disposed below the external channel 1028. The dielectric material 1021 separates the hard magnetic layer 1036 from the external channel 1028. For example, the hard magnetic layer 1036 may have a perpendicular magnetization as shown in FIG. 10. For example, the hard magnetic layer 1036 may be made from a metal material, such as Cobalt (Co), Platinum (Pt), Palladium (Pd), Iron (Fe), Chromium (Cr), multiple alternative layers of CoPt ("CoPt multi-layer"), CoPd, Co Nickel (Ni) (CoNi), Terbium (Tb) Co (TbCo), TbFeCo, CoPd, FePt, and CoCrPt, as non-limiting examples. The hard magnetic layer 1036 is configured to generate the magnetic bias field 1038 in the external channel 1028 to align the magnetic moment of magnetic nanoparticles 1014 disposed in the external channel 1028. In this example, the external channel 1028 extends lower in the TMR sensor 1000 than in the TMR sensor 400 in FIG. 4 for example, so that the magnetic nanoparticles 1014 disposed in the external channel 1028 can be exposed to the magnetic bias field 1038 generated by the hard magnetic layer 1036. In this manner, an external magnetic field generator, such as a coil for example, is not required to be provided to generate the magnetic bias field 1038 in the external channel 1028 to align the magnetic moment of magnetic nanoparticles 1014 disposed in the external channel 1028. Thus, the magnetic bias field 1038 can be provided in the TMR sensor 1000 on-chip, in the biochip 1020 for example.

Also, as another example with reference to the TMR sensor 1000 in FIG. 10, by providing the external channel 1028 between the first and second TMR devices 1002(1), 1002(2), the magnetic stray field 1012(1), 1012(2) generated by the magnetic nanoparticles 1014 can more easily rotate the magnetic moment orientation of the free layers 1008(1), 1008(2) in the first and second TMR devices 1002(1), 1002(2) for a given stray magnetic strength. This is due to reduced distance between the free layers 1008(1), 1008(2) and the magnetic nanoparticles 1014 when disposed in the external channel 1028, thereby further increasing the signal-to-noise ratio (SNR) of the TMR sensor 1000.

Figure 11:
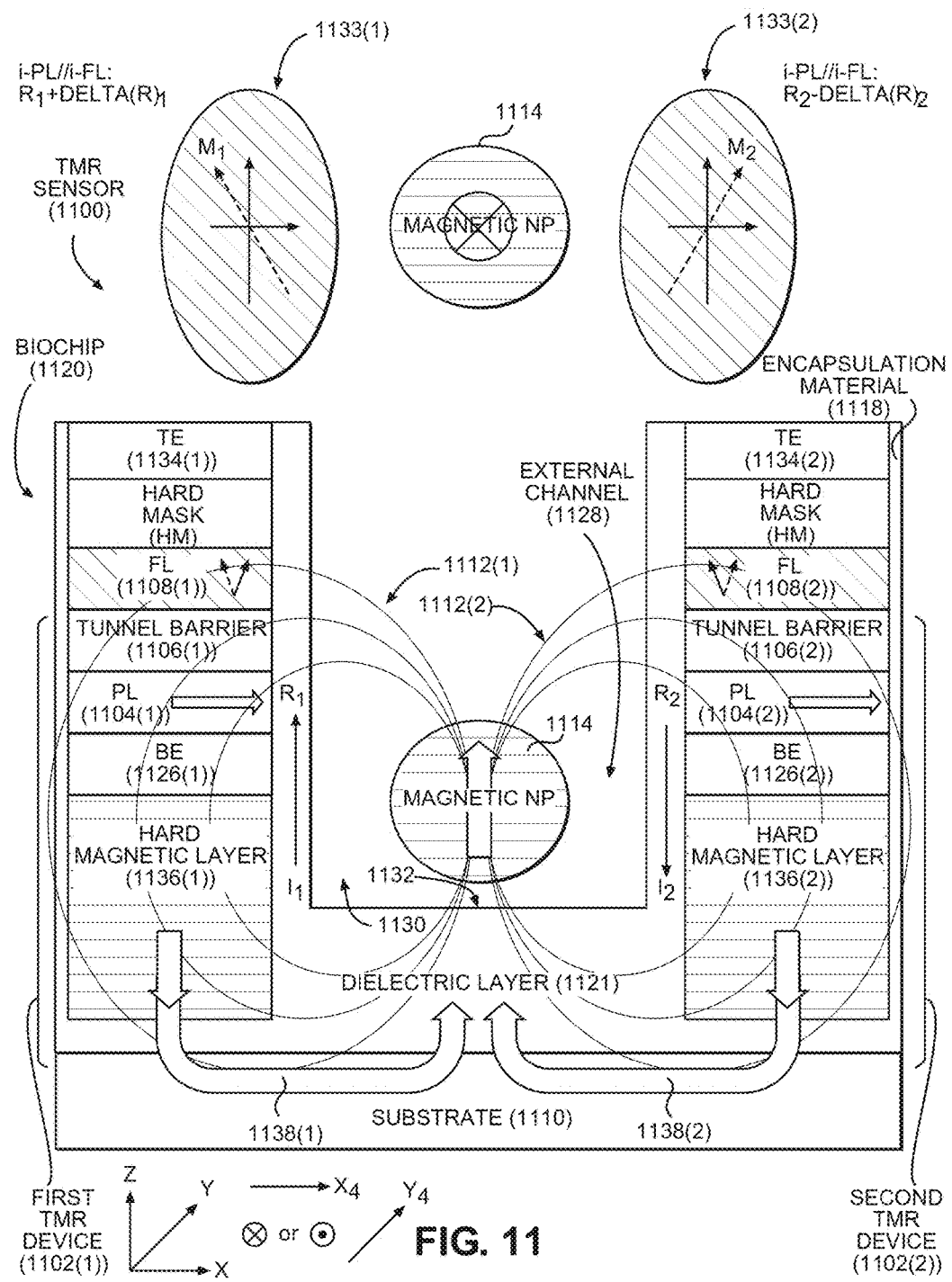
FIG. 11 is a schematic diagram of another exemplary TMR sensor employing dual TMR devices configured to provide differential MR sensing of resistance change in response to the presence of magnetic nanoparticles in a channel disposed between the TMR devices based on a TMR effect, wherein the TMR devices further include hard magnetic layers disposed beneath a tunnel barrier to generate a magnetic bias field in the channel to align magnetic moments of the magnetic nanoparticles disposed therein.

FIG. 11 is a schematic diagram of another exemplary TMR sensor 1100 employing dual TMR devices 1102(1), 1102(2) configured to provide differential MR sensing of resistance change in response to the presence of magnetic nanoparticles 1114 in an external channel 1128 similar to the TMR sensor 400 in FIG. 4. However, in this example, a hard magnetic layer 1136 is disposed beneath an external channel 1128 and outside of the TMR devices 1102(1), 1102(2) to generate a magnetic bias field 1138 in the external channel 1128 to align the magnetic moments of the magnetic nanoparticles 1114 disposed therein.

As shown in FIG. 11, the TMR sensor 1100 employs dual, first and second TMR devices 1102(1), 1102(2) that are MR devices. Note however, that more than two TMR devices 1102 could be provided. The TMR sensor 1100 may be provided in an IC biosensor chip 1120. As will be discussed in more detail below, the first and second TMR devices 1102(1), 1102(2) are configured to provide differential MR sensing of resistance change in response to the presence of magnetic nanoparticles 1114, which may be bound to a bioreceptor that is bound to a target analyte of interest, in the external channel 1128 disposed between the TMR devices 1102(1), 1102(2). The external channel 1128 is formed in a void 1130 in an encapsulation material 1118 such that the external channel 1128 can capture magnetic nanoparticles 1114 without the magnetic nanoparticles 1114 physically contacting the internal components of the first and second TMR devices 1102(1), 1102(2). The first and second TMR devices 1102(1), 1102(2) are disposed on a substrate 1110 and disposed in the encapsulation material 1118 which may include a dielectric material 1121, formed above the substrate 1110. The X, Y, and Z coordinates of the first and second TMR devices 1102(1), 1102(2) are shown in FIG. 11. The X and Y coordinates are in-plane to the first and second TMR devices 1102(1), 1102(2). The Z coordinate is out-of-plane to the first and second TMR devices 1102(1), 1102(2).

The first and second TMR devices 1102(1), 1102(2) each have first and second resistances $R_1$, $R_2$, respectively, based on their layer stackup of the first TMR device 1102(1). In this regard, the first TMR device 1102(1) has a first pinned layer 1104(1) having a first magnetization in a first direction $X_4$. The first pinned layer 1104(1) is disposed above and in electrical contact with a first bottom electrode 1126(1). A first spacer comprised of a first tunnel barrier 1106(1) made from an insulating material (e.g., Aluminum Oxide (AlOx) or Magnesium Oxide (MgO)) is disposed above the first pinned layer 1104(1). A first free layer 1108(1) is disposed above the first tunnel barrier 1106(1) having a first magnetization in a second direction $Y_4$ orthogonal to the first direction opposite of direction $X_4$. Thus, the first tunnel barrier 1106(1) forms an MTJ. The magnetic moment of the first free layer 1108(1) is configured to rotate from the second direction $Y_4$ towards the first direction $X_4$ in response to the presence of the magnetic nanoparticles 1114 in the external channel 1128 exerting a magnetic stray field 1112(1) on the first free layer 1108(1). A bottom surface 1132 of the external channel 1128 is disposed in a horizontal plane adjacent to the first TMR device 1102(1) so that the magnetic stray field 1112(1) generated by the magnetic nanoparticles 1114 reaches the first free layer 1108(1), thereby causing the magnetic moment of the first free layer 1108(1) to rotate. This rotation of the magnetic moment of the first free layer 1108(1) causes the magnetization of the first free layer 1108(1) to change with respect to the magnetization of the first pinned layer 1104(1). In response, the first resistance $R_1$ of the first TMR device 1102(1) increases as a result of exerting the magnetic stray field 1112(1) on the first free layer 1108(1). Note that in this example, the bottom surface 1132 of the external channel 1128 extends below the horizontal plane of the first free layer 1108(1).

Similarly, with continuing reference to FIG. 11, the second TMR device 1102(2) has a second pinned layer 1104(2) having a first magnetization in the first direction $X_4$. The second pinned layer 1104(2) is disposed above and in electrical contact with a second bottom electrode 1126(2). A first spacer comprised of a second tunnel barrier 1106(2) made from an insulating material (e.g., Aluminum Oxide (AlOx) or Magnesium Oxide (MgO)) is disposed above the second pinned layer 1104(2). A second free layer 1108(2) is disposed above the second tunnel barrier 1106(2) having the second magnetization in the second direction $Y_4$ perpendicular to the first direction $X_4$. Thus, the second tunnel barrier 1106(2) forms an MTJ. The second free layer 1108(2) is configured to rotate from the second direction $Y_4$ towards the first direction $X_4$ opposite from the rotation of the first free layer 1108(1) in response to the presence of the magnetic nanoparticles 1114 in the external channel 1128 exerting a magnetic stray field 1112(2) on the second free layer 1108(2). This rotation of the magnetic moment of the second free layer 1108(2) causes the magnetization of the second free layer 1108(2) to change with respect to the magnetization of the second pinned layer 1104(2). In response, the second resistance $R_2$ of the second TMR device 1102(2) decreases as a result of exerting the magnetic stray field 1112(1) on the second free layer 1108(2).

Note that the first and second TMR devices 1102(1), 1102(2) could alternatively be fabricated such that their first and second free layers 1108(1), 1108(2) are disposed below the first and second tunnel barriers 1106(1), 1106(2), and their first and second pinned layers 1104(1), 1104(2) be disposed above the first and second tunnel barriers 1106(1), 1106(2).

The first and second TMR devices 1102(1), 1102(2) in the TMR sensor 1100 in FIG. 11 can provide differential sensing of the magnetic nanoparticles 1114 to improve the SNR of the TMR sensor 1100, because the first and second resistances $R_1$, $R_2$ of the first and second TMR devices 1102(1), 1102(2) are arranged such that the first and second resistances $R_1$, $R_2$ change in opposite manners in response to the presence of the magnetic nanoparticles 1114. For example, in the TMR sensor 1100 in FIG. 11, the first resistance $R_1$ of the first TMR device 1102(1) is configured to increase by a certain first delta resistance $DELTA(R)_1$ (e.g., in the range of micro-Ohms or nano-Ohms) as shown in a top-view magnetization diagram 1133(1) as the orthogonal magnetization of the first free layer 1108(1) changes to the $M_1$ magnetization. The second resistance $R_1$ of the second TMR device 1102(2) is configured to decrease by a certain second delta resistance $DELTA(R)_2$ (e.g., in the range of micro-Ohms or nano-Ohms), as shown in a top-view magnetization diagram 1133(2) as the as the orthogonal magnetization of the second free layer 1108(2) changes to the $M_2$ magnetization. The first delta resistance $DELTA(R)_1$ and the second delta resistance $DELTA(R)_2$ may be approximately equal. Further, the first and second resistances $R_1$, $R_2$ may be approximately equal.

With continuing reference to FIG. 11, the first and second TMR devices 1102(1), 1102(2) are disposed between and in electrical contact with respective bottom and top electrodes. In this regard, the first bottom electrode 1126(1) is disposed below and in electrical contact with the first TMR device 1102(1), and the first pinned layer 1104(1) in this example. A first top electrode 1134(1) is disposed above and also in electrical contact with the first TMR device 1102(1), and the first free layer 1108(1) in this example. Thus, the first TMR device 1102(1) is configured to carry a first current L between the first bottom electrode 1126(1) and the first top electrode 1134(1) in response to a first voltage differential applied between the first bottom electrode 1126(1) and the first top electrode 1134(1) based on the first resistance $R_1$ of the first TMR device 1102(1). The second bottom electrode 1126(2) is disposed below and in electrical contact with the second TMR device 1102(2), and the second pinned layer 1104(2) in this example. A second top electrode 1134(2) is disposed above and also in electrical contact with the second TMR device 1102(2), and the second free layer 1108(2) in this example. The second TMR device 1102(2) is configured to carry a second current $I_2$ between the second bottom electrode 1126(2) and the second top electrode 1134(2) in response to a second voltage differential applied between the second bottom electrode 1126(2) and the second top electrode 1134(2) based on the second resistance $R_2$ of the second TMR device 1102(2). As will be discussed below, these currents $I_1$, $I_2$ can be sensed to generate differential signals indicative of the differential change in resistances $R_1$, $R_2$ in the first and second TMR devices 1102(1), 1102(2) in response to the magnetic nanoparticles 1114.

To provide for the ability to generate a magnetic bias field in the external channel 1128 to align the magnetic moment of the magnetic nanoparticles 1114, first and second hard magnetic layers 1136(1), 1136(2) is provided in the TMR sensor 1100. In this example, the first and second hard magnetic layers 1136(1), 1136(2) are disposed below the external channel 1128 and below the bottom electrodes 1126(1), 1126(2) in the TMR devices 1102(1), 1102(2). For example, the first and second hard magnetic layers 1136(1), 1136(2) may have a perpendicular magnetization as shown in FIG. 10. For example, the first and second hard magnetic layers 1036(1), 1036(2) may be made from a metal material, such as Cobalt (Co), Platinum (Pt), Palladium (Pd), Iron (Fe), Chromium (Cr), CoPt, multiple alternative layers of CoPt ("CoPt multi-layer"), CoPd, Co Nickel (Ni) (CoNi), Terbium (Tb) Co (TbCo), TbFeCo, CoNi, TbCo, TbFeCo, FePt, and CoCrPt, as non-limiting examples. The hard magnetic layers 1036(1), 1036(2) are configured to generate first and second magnetic bias fields 1138(1), 1138(2) in the first and second hard magnetic layers 1136(1), 1136(2) to align the magnetic moment of magnetic nanoparticles 1114 disposed in the external channel 1128. In this example, the external channel 1128 extends lower in the TMR sensor 1100 than in the TMR sensor 400 in FIG. 4 for example, so that the magnetic nanoparticles 1114 disposed in the external channel 1128 can be exposed to the first and second magnetic bias fields 1038(1), 1038(2) generated by the first and second hard magnetic layers 1136(1), 1136(2) disposed lower in the TMR sensor 1100. In this manner, an external magnetic field generator, such as a coil for example, is not required to be provided to generate a magnetic bias field 1138(1), 1138(2) in the external channel 1128 to align the magnetic moment of magnetic nanoparticles 1114 disposed in the external channel 1128. Thus, the first and second magnetic bias fields 1138(1), 1138(2) can be provided in the TMR sensor 1100 on-chip, in the biochip 1120 for example.

Also, as another example with reference to the TMR sensor 1100 in FIG. 11, by providing the external channel 1128 between the first and second TMR devices 1102(1), 1102(2), the magnetic stray field 1112(1), 1112(2) generated by the magnetic nanoparticles 1114 can more easily rotate the magnetic moment orientation of the free layers 1108(1), 1108(2) in the first and second TMR devices 1102(1), 1102(2) for a given stray magnetic strength. This is due to reduced distance between the free layers 1108(1), 1108(2) and the magnetic nanoparticles 1114 when disposed in the external channel 1128, thereby further increasing the signal-to-noise ratio (SNR) of the TMR sensor 1100.

Figure 12:
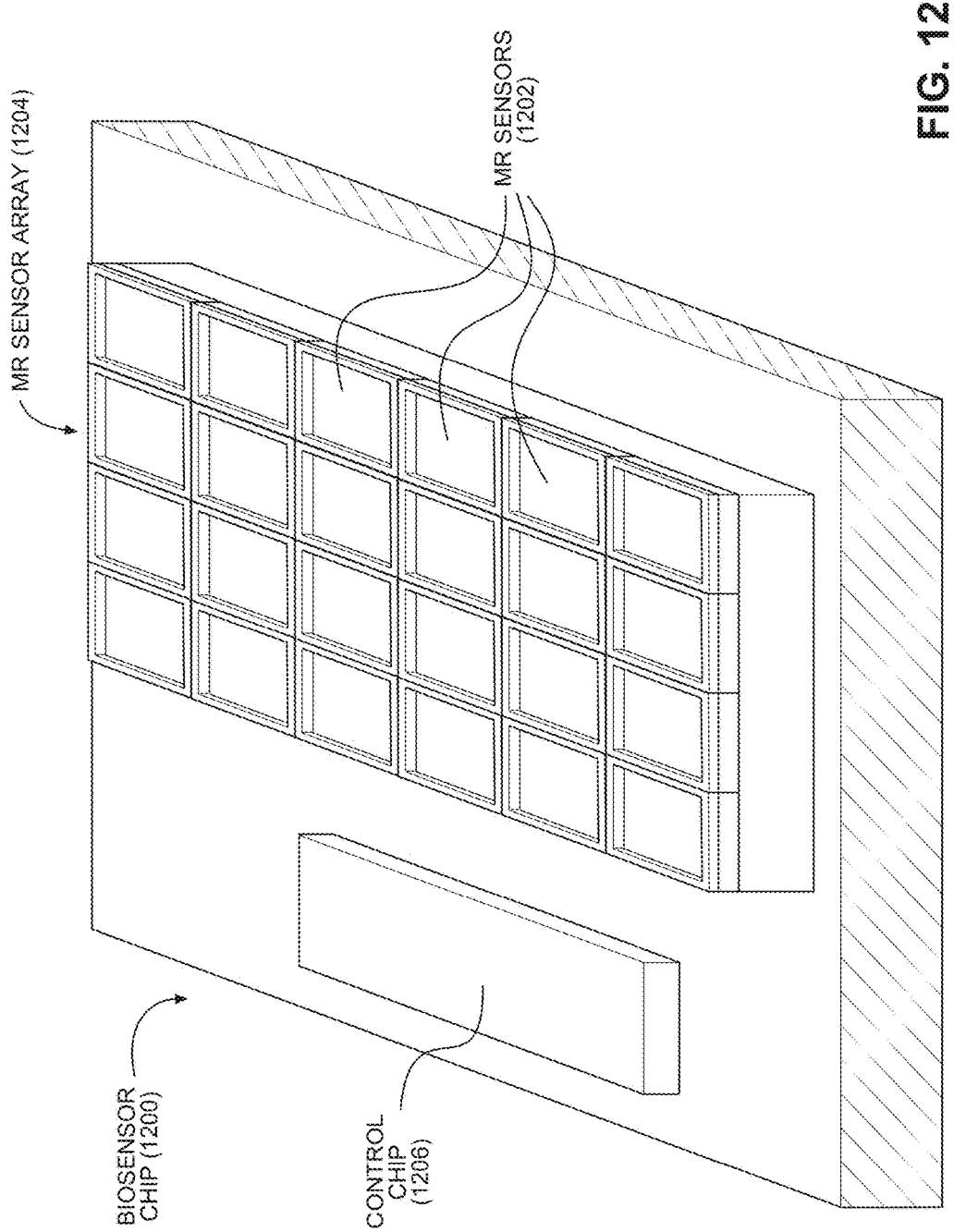
FIG. 12 is an exemplary biosensor chip that can employ one or more MR sensors employing dual MR devices configured to provide differential MR sensing of resistance change in response to the presence of magnetic nanoparticles, which may be bound to a bioreceptor that is bound to a target analyte of interest, in a channel disposed between the MR devices, based on a MR effect.

FIG. 12 is an exemplary biosensor chip 1200 that can employ one or more MR sensors 1202, such as TMR and GMR sensors 400, 900, 1000, and 1100 as examples, each employing dual MR devices configured to provide differential MR sensing of resistance change in response to the presence of magnetic nanoparticles. The biosensor chip 1200 may be provided in different applications, including wearable devices, point-of-care devices for point-of-care applications, a bacteria inflection diagnostics device for bacteria infection detection applications, a cancer detection device for cancer detection, a heart disease diagnostic device for detecting heart disease, a food safety monitoring device for food monitoring applications, etc. The magnetic nanoparticles may be bound to a bioreceptor that is bound to a target analyte of interest, in a channel disposed between the MR devices, based on a MR effect. As shown in FIG. 12, the biosensor chip 1200 may have an MR sensor array 1204 that contains a plurality of MR sensors 1202. A control chip 1206 may also be provided in the biosensor chip 1200 that controls the sensing operation of the biosensor chip 1200. For example, the control chip 1206 may include components in the MR sensing system 700 in FIG. 7, including the sensing circuit 706 and the sense amplifier 708.

Those of skill in the art will further appreciate that the various illustrative logical blocks, modules, circuits, and algorithms described in connection with the aspects disclosed herein may be implemented as electronic hardware, instructions stored in memory or in another computer-readable medium and executed by a processor or other processing device, or combinations of both. The master devices and slave devices described herein may be employed in any circuit, hardware component, integrated circuit (IC), or IC chip, as examples. Memory disclosed herein may be any type and size of memory and may be configured to store any type of information desired. To clearly illustrate this interchangeability, various illustrative components, blocks, modules, circuits, and steps have been described above generally in terms of their functionality. How such functionality is implemented depends upon the particular application, design choices, and/or design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the aspects disclosed herein may be implemented or performed with a processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A processor may be a microprocessor, but in the alternative, the processor may be any processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The aspects disclosed herein may be embodied in hardware and in instructions that are stored in hardware, and may reside, for example, in Random Access Memory (RAM), flash memory, Read Only Memory (ROM), Electrically Programmable ROM (EPROM), Electrically Erasable Programmable ROM (EEPROM), registers, a hard disk, a removable disk, a CD-ROM, or any other form of computer readable medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a remote station. In the alternative, the processor and the storage medium may reside as discrete components in a remote station, base station, or server.

It is also noted that the operational steps described in any of the exemplary aspects herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary aspects may be combined. It is to be understood that the operational steps illustrated in the flow chart diagrams may be subject to numerous different modifications as will be readily apparent to one of skill in the art. Those of skill in the art will also understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

What is claimed is:

1. A magnetoresistive (MR) sensor, comprising:
    a first MR device disposed in an encapsulation material, the first MR device having a first resistance;
    a second MR device disposed in the encapsulation material a horizontal distance away from the first MR device, the second MR device having a second resistance; and
    an external channel formed in a void in the encapsulation material between the first MR device and the second MR device, the external channel configured to capture magnetic nanoparticles;
    the first resistance of the first MR device configured to increase in response to a presence of the magnetic nanoparticles in the external channel exerting a magnetic stray field on the first MR device; and
    the second resistance of the second MR device configured to decrease in response to the presence of the magnetic nanoparticles in the external channel exerting the magnetic stray field on the second MR device.

2. The MR sensor of claim 1, wherein a magnitude of the increase in the first resistance in response to the presence of the magnetic nanoparticles in the external channel exerting the magnetic stray field on the first MR device is approximately equal to a magnitude of the decrease in the second resistance in response to the presence of the magnetic nanoparticles in the external channel exerting the magnetic stray field on the second MR device.

3. The MR sensor of claim 1, wherein a bottom surface of the external channel is disposed in a horizontal plane adjacent to the first MR device and the second MR device.

4. The MR sensor of claim 1, further comprising a passivation layer;
    the first MR device disposed in the passivation layer; and
    the second MR device disposed in the passivation layer.

5. The MR sensor of claim 1, wherein:
    the first MR device comprises:
        a first pinned layer having a first magnetization in a first direction;
        a first spacer disposed above the first pinned layer; and
        a first free layer disposed above the first spacer having a first magnetization in a second axis orthogonal to the first direction;
        the first free layer configured to rotate about the second axis in the first direction in response to the presence of the magnetic nanoparticles in the external channel exerting the magnetic stray field on the first free layer; and
    the second MR device comprises:
        a second pinned layer having the first magnetization in the first direction;
        a second spacer disposed above the second pinned layer; and
        a second free layer disposed above the second spacer having a second magnetization in a second direction;
        the second free layer configured to rotate about the second axis in the second direction opposite of the first direction in response to the presence of the magnetic nanoparticles in the external channel exerting the magnetic stray field on the second free layer.

6. The MR sensor of claim 5, wherein a bottom surface of the external channel is disposed in a horizontal plane below the first free layer and the second free layer.

7. The MR sensor of claim 1, wherein:
    the first MR device comprises:
        a first free layer having a first magnetization in a second axis;
        a first spacer disposed above the first free layer; and
        a first pinned layer disposed above the first spacer, the first pinned layer having the first magnetization in a first direction orthogonal to the second axis;
        the first free layer configured to rotate about the second axis in a first direction in response to the presence of the magnetic nanoparticles in the external channel exerting the magnetic stray field on the first free layer; and
    the second MR device comprises:
        a second free layer having the first magnetization in the second axis;
        a second spacer disposed above the second free layer; and
        a second pinned layer disposed above the second spacer, the second pinned layer having the first magnetization in the first direction orthogonal to the second axis;

the second free layer configured to rotate about the second axis in a second direction opposite of the first direction in response to the presence of the magnetic nanoparticles in the external channel exerting the magnetic stray field on the second free layer.

8. The MR sensor of claim 7, wherein a bottom surface of the external channel is disposed in a horizontal plane below the first free layer and the second free layer.

9. The MR sensor of claim 1, further comprising:
a first bottom electrode disposed below and in electrical contact with the first MR device;
a first top electrode disposed above and in electrical contact with the first MR device;
a second bottom electrode disposed below and in electrical contact with the second MR device; and
a second top electrode disposed above and in electrical contact with the second MR device;
the first MR device configured to carry a first current between the first bottom electrode and the first top electrode in response to a first voltage differential applied between the first bottom electrode and the first top electrode based on the first resistance of the first MR device; and
the second MR device configured to carry a second current between the second bottom electrode and the second top electrode in response to a second voltage differential applied between the second bottom electrode and the second top electrode based on the second resistance of the second MR device.

10. The MR sensor of claim 1, wherein:
the first MR device further comprises a first hard magnetic layer having a perpendicular magnetization disposed adjacent to the external channel, the first hard magnetic layer configured to generate a first magnetic bias field in the external channel to align a magnetic moment of the magnetic nanoparticles disposed in the external channel; and
the second MR device further comprises a second hard magnetic layer having the perpendicular magnetization disposed adjacent to the external channel, the second hard magnetic layer configured to generate a second magnetic bias field in the external channel to align the magnetic moment of the magnetic nanoparticles disposed in the external channel.

11. The MR sensor of claim 10, wherein the first hard magnetic layer is configured to generate the first magnetic bias field in the external channel having a south to north direction, and the second hard magnetic layer is configured to generate the second magnetic bias field in the external channel in a north to south direction.

12. The MR sensor of claim 10, wherein the first hard magnetic layer is configured to generate the first magnetic bias field in the external channel having a north to south direction, and the second hard magnetic layer is configured to generate the second magnetic bias field in the external channel in a north to south direction.

13. The MR sensor of claim 10, wherein:
the first hard magnetic layer comprises a first material comprised from the group consisting of Cobalt (Co), Platinum (Pt), Palladium (Pd), Iron (Fe), Chromium (Cr), CoPt, multiple alternative layers of CoPt ("CoPt multi-layer"), CoPd, Co Nickel (Ni) (CoNi), Terbium (Tb) Co (TbCo), TbFeCo, FePt, and CoCrPt; and
the second hard magnetic layer comprises a second material comprised from the group consisting of Cobalt (Co), Platinum (Pt), Palladium (Pd), Iron (Fe), Chromium (Cr), multiple alternative layers of CoPt ("CoPt multi-layer"), CoPd, Co Nickel (Ni) (CoNi), Terbium (Tb) Co (TbCo), TbFeCo, CoPt, CoPd, FePt, and CoCrPt.

14. The MR sensor of claim 1, further comprising a hard magnetic layer having a perpendicular magnetization disposed below the external channel, the hard magnetic layer configured to generate a magnetic bias field in the external channel to align a magnetic moment of the magnetic nanoparticles disposed in the external channel.

15. The MR sensor of claim 14, wherein the hard magnetic layer is configured to generate the magnetic bias field in the external channel having a north to south direction.

16. The MR sensor of claim 14, further comprising a dielectric material layer disposed between the hard magnetic layer and the external channel.

17. The MR sensor of claim 5, wherein:
the first MR device comprises a first tunnel magnetoresistive (TMR) device;
the first spacer of the first TMR device comprises a first tunnel barrier;
the second MR device comprises a second TMR device; and
the second spacer of the second TMR device comprises a second tunnel barrier;
the first resistance of the first TMR device is configured to increase in response to the presence of the magnetic nanoparticles in the external channel exerting the magnetic stray field on the first TMR device in response to a TMR effect; and
the second resistance of the second TMR device is configured to decrease in response to the presence of the magnetic nanoparticles in the external channel exerting the magnetic stray field on the second TMR device in response to the TMR effect.

18. The MR sensor of claim 5, wherein:
the first MR device comprises a first giant magnetoresistive (GMR) device;
the first spacer of the first GMR device comprises a first metal spacer;
the second MR device comprises a second GMR device; and
the second spacer of the second GMR device comprises a second metal spacer;
the first resistance of the first GMR device is configured to increase in response to the presence of the magnetic nanoparticles in the external channel exerting the magnetic stray field on the first GMR device in response to a GMR effect; and
the second resistance of the second GMR device is configured to decrease in response to the presence of the magnetic nanoparticles in the external channel exerting the magnetic stray field on the second GMR device in response to the GMR effect.

19. The MR sensor of claim 9, further comprising:
a first access transistor comprising a first gate, a first electrode, and a second electrode,
wherein:
the first gate of the first access transistor is coupled to a word line;
the first bottom electrode of the first MR device is coupled to the first electrode of the first access transistor; and
the first top electrode of the first MR device is coupled to a selector line;
the first MR device configured to receive the first current between the first top electrode and the first bottom electrode based on the first resistance of the first MR device, in response to a control signal on the word line activating the first access transistor and a first voltage applied to the selector line; and a second access transistor comprising a second gate, a first electrode, and a second electrode, wherein:
- the second gate of the second access transistor is coupled to the word line;
- the second bottom electrode of the second MR device is coupled to the first electrode of the second access transistor; and
- the second top electrode of the second MR device is coupled to the selector line;

the second MR device configured to receive the second current between the second top electrode and the second bottom electrode based on the second resistance of the second MR device in response to the control signal on the word line activating the second access transistor and a second voltage applied to the selector line.

20. The MR sensor of claim 1, comprising an MR biosensor configured to capture the magnetic nanoparticles bound to a bioreceptor bound to a target analyte of a biological sample.

21. The MR sensor of claim 1 integrated into an integrated circuit (IC) chip.

22. The MR sensor of claim 1 integrated into a device selected from the group consisting of: a wearable device, a point-of-care device, a bacteria infection diagnostic device, a cancer detection device, a heart disease diagnostic device, and a food safety monitoring device.

23. A magnetoresistive (MR) sensor, comprising:
- a first means for providing a first MR resistance disposed in an encapsulation material;
- a second means for providing a second MR resistance disposed in the encapsulation material a horizontal distance away from the first means for providing the first MR resistance; and
- a means for capturing external magnetic nanoparticles between the first means for providing the first MR resistance and the second means for providing the second MR resistance;
- the first means for providing the first MR resistance increasing in resistance in response to the presence of the magnetic nanoparticles in an external channel exerting a magnetic stray field on the first means for providing the first MR resistance; and
- the second means for providing the second MR resistance decreasing in resistance in response to the presence of the magnetic nanoparticles in the external channel exerting the magnetic stray field on the second means for providing the second MR resistance.

* * * * *